(12) United States Patent
Pederson et al.

(10) Patent No.: US 7,598,059 B2
(45) Date of Patent: Oct. 6, 2009

(54) NEUBLASTIN EXPRESSION CONSTRUCTS

(75) Inventors: Nels E. Pederson, Mansfield, MA (US); William P. Sisk, Boxborough, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 389 days.

(21) Appl. No.: 10/957,221

(22) Filed: Oct. 1, 2004

(65) Prior Publication Data

US 2005/0158824 A1  Jul. 21, 2005

Related U.S. Application Data

(60) Provisional application No. 60/507,483, filed on Oct. 2, 2003.

(51) Int. Cl.
| | |
|---|---|
| C12N 15/12 | (2006.01) |
| C12N 15/62 | (2006.01) |
| C12N 15/63 | (2006.01) |
| C07H 21/00 | (2006.01) |

(52) U.S. Cl. ............... 435/69.8; 435/69.1; 435/325; 435/358; 435/320.1; 536/23.4; 536/23.51

(58) Field of Classification Search .............. None
See application file for complete search history.

(56) References Cited

U.S. PATENT DOCUMENTS

| 6,083,725 | A | * | 7/2000 | Selden et al. ............... 435/69.8 |
|---|---|---|---|---|
| 6,361,771 | B1 | | 3/2002 | Tao et al. |
| 2002/0002269 | A1 | | 1/2002 | Milbrandt et al. |
| 2002/0055467 | A1 | * | 5/2002 | Johansen et al. ............... 514/12 |
| 2005/0089960 | A1 | | 4/2005 | Wahlberg et al. |
| 2007/0238650 | A1 | | 10/2007 | Sah et al. |

FOREIGN PATENT DOCUMENTS

| WO | WO 93/06116 | 4/1993 |
|---|---|---|
| WO | WO 97/08196 | 3/1997 |
| WO | WO99/13090 | 3/1999 |
| WO | WO 00/01815 | 1/2000 |
| WO | WO 00/04050 | 1/2000 |
| WO | WO 00/18799 | 4/2000 |
| WO | WO 01/47946 | 7/2001 |
| WO | WO02/46430 | 6/2002 |
| WO | WO 02/051433 | 7/2002 |
| WO | WO 02/060929 | 8/2002 |
| WO | WO 02/072826 | 9/2002 |
| WO | WO 02/078730 | 10/2002 |
| WO | WO 2004/094592 | 11/2004 |
| WO | WO 2004/108760 | 12/2004 |
| WO | WO 2005/039643 | 5/2005 |

OTHER PUBLICATIONS

Wang et al. World Journal of Gastroenterology. 8(2): 253-257, 2002.*
Andres et al. (2001) "Multiple effects of artemin on sympathetic neurone generation, survival and growth," Development 128:3685-3695.
Aebischer et al. (1996) "Intrathecal delivery of CNTF using encapsulated genetically modified xenogeneic cells in amyotrophic lateral sclerosis patients," Nature Medicine, 2:696-699.
Aebischer et al (2001) "Recombinant proteins for neurodegenerative diseases: the delivery issue," Trends in Neuroscience, Elsevier, Amsterdam, NL 24(9):533-540.
Baloh et al. (1998) "Artemin, a novel member of the GDNF Ligand family, supports peripheral and central neurons and signals through the GFRα3-RET Receptor complex," Neuron 21:1291-1302.
Baloh et al. (2000) "Functional mapping of receptor specificity domains of glial cell line-derived neurothropic factor (GDNF) family ligands and production of GFR alpha 1 RET-specific agonists," J. of Biological Chemistry 275(5):3412-3420.
Baudet et al. (2000) "Positive and negative interactions of GDNF, NTN and ART in developing sensory neuron subpopulations, and their collaboration with neurotrophins," Development 127:4335-4344.
Bauskin et al. (2000) "The propeptide of macrophage inhibitory cytokine (MIC-1), a TGF-β superfamily member, acts as a quality control determinant for correctly folded MIC-1," The EMBO Journal 19(10):2212-2220.
Bendtsen et al. (2004) "Improved prediction of signal peptides—SignalP 3.0," J. Mol. Biol. 340(4):783-795.
Bootcov et al. (1997) "MIC-1, a novel macrophage inhibitory cytokine, is a divergent member of the TGF-β superfamily," PNAS, Immunology, Cell Biology 94:11514-11519.
Enomoto et al. (2001) "RET signaling is essential for migration, axonal growth and axon guidance of developing sympathetic neurons," Development 128:3963-3974.
Fairlie et al. (2001) "The propeptide of the transforming growth factor-β superfamily member, macrophage inhibitory cytokine-1 (MIC-1), is a multifunctional domain that can facilitate protein folding and secretion," J. of Biol. Chem. 276(20):16911-16918.

(Continued)

*Primary Examiner*—Christine J Saoud
(74) *Attorney, Agent, or Firm*—Fish & Richardson P.C.

(57) ABSTRACT

A method of producing a secreted neublastin polypeptide using a heterologous signal sequence is disclosed. The secreted neublastin does not contain a neublastin pro sequence.

18 Claims, 9 Drawing Sheets

OTHER PUBLICATIONS

Flanders et al. "TGFβ," Laboratory of Cell Regulation and Carcinogenesis, National Cancer Institute pp. 719-746.
Griffin et al. (2001) "Assessment of cutaneous innervation by skin biopsies," Current Opinion in Neurology 14:655-659.
Hoane et al. (2000) "Mammalian-Cell-Produced Neurturin (NTN) Is More Potent Than Purified *Escherichia coli*-Produced NTN," Exp. Neurol. 162:189-193.
Li et al. (2003)"Expression, purification, and characterization of recombinant human neurturin secreted from the yeast *Pichia pastoris*," Protein expression and purification 30(1):11-17.
Milbrandt et al. (1998) "Persephin, a novel neurotrophic factor related to GDNF and Neurturin," Neuron 20:245-253.
Moustakas et al. (2001) "Smad regulation in TGF-β signal transduction," J. of Cell Science 114:4359-4369.
Nielsen et al. (1997) "Identification of prokaryotic and eukaryotic signal peptides and prediction of their cleavage sites," Protein Engineering 10(1):1-6.
Nielsen et al. (1998) "Prediction of signal peptides and signal anchors by a hidden Markov model," Proceedings of the 6th International Conference on Intelligent systems for Molecular Biology, pp. 122-130.
Nishino et al. (1999) "GFR alpha3, a component of the artemin receptor, is required for migration and survival of the superior cervical ganglion," Neuron 23(4):725-736.
Rattenholl et al. (2001) "The pro-sequence facilitates folding of human nerve growth factor from *Escherichia coli* inclusion bodies," Eur. J. Biochem. 268:3296-3303.
Rattenholl et al. (2001) "Pro-sequence assisted folding and disulfide bond formation of human nerve growth factor," J. Mol. Biol. 305:523-533.
Reinshagen et al. (2000) "Commercial recombinant human β-Nerve Growth factor and adult rat dorsal root ganglia contain an identical molecular species of nerve growth factor prohormone," J. of Neurochemistry 74:2127-2133.
Rosenblad et al. (2000) "In vivo protection of nigral dopamine neurons by lentiviral gene transfer of the novel GDNF-family member neublastin/artemin," Molecular and Cellular Neuroscience 15(2):199-214.
Rosenblad et al. (2001) "In vivo protection of nigral dopamine neurons by lentiviral gene transfer of the novel GDNF-family member neublastin/artemin," Mol. Cell Neurosci. 18(3):332-333.
Saarma et al. (1999) "Other neurotrophic factors: glial cell line-derived neurotrophic factor (GDNF)," Microsc. Res. Tech. 45(4-5):292-302.
Saarma, M. (2000) "GDNF: A stranger in the TGF-beta superfamily?" European Journal of Biochemistry 267(24):6968-6971.
Tseng et al. (1998) "Neurturin protects dopaminergic neurons following medial forebrain bundle axotomy," Mol. Neurosci 9:1817-1822.
Bonde et al., "GDNF and neublastin protect against NMDA-induced excitotoxicity in hipocampal slice cultures," Neuroreport 11:4069-4073 (2000).
Bork, "Go hunting in sequence databases but watch out of the traps," Trends in Genetics 12:425-427 (1996).
Bork, "Powers and Pitfalls in Sequence analysis: the 70% Hurdle," Genome Research 10:398-400 (2000).
Brenner "Errors in genome annotation," Trends in Genetics 15:132-133 (1999).
Doerks et al. "Protein annotation: detective work for function prediction," Trends in Genetics 14:248-250 (1998).
Fjord-Larsen, L. et al. "Efficient in vivo protection of nigral dopaminergic neurons by lentiviral gene transfer of a modified Neurturin construct," Experimental Neurology, pp. 49-60 (2005).
Merlo et al. "The Mouse *int-2* Gene Exhibits Basic Fribroblast Growth Facctor Activity in a Basic Fibroblast Growth Factor-responsive Cell Line," Cell Growth & Differentiation 1:463-472 (1990).
Skolnick et al. "From genes to protein structure and function: novel applications of computational approaches in the genomic era," Trends in Biotech. 18(1):34-39 (2000).
Smith et al. The challenges of genome sequence annotation or "The devil is in the details," Nature Biotechnology 15:1222-1223 (1997).
Wells, "Additivity of Mutational Effects in Proteins," Biochemistry 29:8509-8517 (1990).
Hall, J. et al., "Eukaryotic and Prokaryotic Signal Peptides Direct Secretion of a Bacterial Endoglucanase by Mammalian Cells," 1990, *Journal of Biological Chemistry*, 265(32):19996-19999.
Maeda, Y. et al., "Efficient Production of Active TNF α By albumin Signal Peptide," 1997, *Biochemistry and Molecular Biology International*, Academic Press, London, GB, 42(4):825-832.
Veronese, F.M. et al., "Introduction and Overview of Peptide and Protein Pegylation," 2002, *Advanced Drug Delivery Reviews*, 54(4):453-456.
Ngo et al., The Protein Folding Problem and Tertiary Structure Prediction, Birkhäuser (1994), pp. 492-495.
Palmitter et al., "Heterologous introns can enhance expression of transgenes in mice," PNAS (1991), 88:478-482.

\* cited by examiner

```
Peptide    Ala Ala Gly Ala Arg Gly Cys Arg Leu Arg Ser Gln Leu Val
Native     GCA GCG GGG GCG CGG GGC TGC CGC CTG CGC TCG CAG CTG GTG
Syn        GCC GCC GGC GCT CGA GGC TGC CGG CTG CGG TCC CAG CTG GTG
Changed    --* --* --* --* --* --- --- --* --- --* --* --- --- ---

Peptide    Pro Val Arg Ala Leu Gly Leu Gly His Arg Ser Asp Glu Leu
Native     CCG GTG CGC GCG CTC GGC CTG GGC CAC CGC TCC GAC GAG CTG
Syn        CCT GTG CGG GCC CTG GGC CTG GGC CAC CGG TCC GAC GAG CTG
Changed    --* --- --* --* --* --- --- --- --- --* --- --- --- ---

Peptide    Val Arg Phe Arg Phe Cys Ser Gly Ser Cys Arg Arg Ala Arg
Native     GTG CGT TTC CGC TTC TGC AGC GGC TCC TGC CGC CGC GCG CGC
Syn        GTG CGG TTC CGG TTC TGC TCC GGC TCC TGC CGG CGG GCC CGG
Changed    --- --* --- --* --- --- **- --- --- --- --* --* --*

Peptide    Ser Pro His Asp Leu Ser Leu Ala Ser Leu Leu Gly Ala Gly
Native     TCT CCA CAC GAC CTC AGC CTG GCC AGC CTA CTG GGC GCC GGG
Syn        TCC CCT CAC GAC CTG TCC CTG GCC TCC CTG CTG GGC GCC GGC
Changed    --* --* --- --- --* **- --- --- **- --* --- --- --- --*

Peptide    Ala Leu Arg Pro Pro Gly Ser Arg Pro Val Ser Gln Pro
Native     GCC CTG CGA CCG CCC CCG GGC TCC CGG CCC GTC AGC CAG CCC
Syn        GCC CTG CGG CCT CCT CCT GGC TCC CGG CCT GTG TCC CAG CCT
Changed    --- --- --* --* --* --* --- --- --- --* --* **- --- --*

Peptide    Cys Cys Arg Pro Thr Arg Tyr Glu Ala Val Ser Phe Met Asp
Native     TGC TGC CGA CCC ACG CGC TAC GAA GCG GTC TCC TTC ATG GAC
Syn        TGC TGC CGG CCT ACC CGG TAC GAG GCC GTG TCC TTC ATG GAC
Changed    --- --- --* --* --* --* --- --* --* --* --- --- --- ---

Peptide    Val Asn Ser Thr Trp Arg Thr Val Asp Arg Leu Ser Ala Thr
Native     GTC AAC AGC ACC TGG AGA ACC GTG GAC CGC CTC TCC GCC ACC
Syn        GTG AAC TCC ACC TGG CGG ACC GTG GAC CGG CTG TCC GCC ACC
Changed    --* --- **- --- --- *-* --- --- --- --* --* --- --- ---

Peptide    Ala Cys Gly Cys Leu Gly
Native     GCC TGC GGC TGC CTG GGC
Syn        GCC TGC GGC TGC CTG GGC
Changed    --- --- --- --- --- ---
```

Fig. 1

```
CGA GGC TGC CGG CTG CGG TCC CAG CTG GTG CCT GTG CGG GCC CTG GGC CTG GGC CAC
Arg Gly Cys Arg Leu Arg Ser Gln Leu Val Pro Val Arg Ala Leu Gly Leu Gly His

CGG TCC GAC GAG CTG GTG CGG TTC CGG TTC TGC TCC GGC TCC TGC CGG CGG GCC CGG
Arg Ser Asp Glu Leu Val Arg Phe Arg Phe Cys Ser Gly Ser Cys Arg Arg Ala Arg

TCC CCT CAC GAC CTG TCC CTG GCC TCC CTG CTG GGC GCC GGC GCC CTG CGG CCT CCT
Ser Pro His Asp Leu Ser Leu Ala Ser Leu Leu Gly Ala Gly Ala Leu Arg Pro Pro

CCT GGC TCC CGG CCT GTG TCC CAG CCT TGC TGC CGG CCT ACC CGG TAC GAG GCC GTG
Pro Gly Ser Arg Pro Val Ser Gln Pro Cys Cys Arg Pro Thr Arg Tyr Glu Ala Val

TCC TTC ATG GAC GTG AAC TCC ACC TGG CGG ACC GTG GAC CGG CTG TCC GCC ACC GCC
Ser Phe Met Asp Val Asn Ser Thr Trp Arg Thr Val Asp Arg Leu Ser Ala Thr Ala

TGC GGC TGC CTG GGC TGA
Cys Gly Cys Leu Gly •••
```

Fig. 2

```
ATG AGC TGG GCC TGG GCG GCC TGT CCA CCC TGT CCC ACT GCC CTT GGC CTC GGC
Met Ser Trp Ala Trp Ala Ala Cys Pro Pro Cys Pro Thr Ala Leu Gly Leu Gly

GGC AGT GCC CTG TGG CCT ACC CTG GCC GCC CTG GCC CTG CTG TCC TCC GTG GCC
Gly Ser Ala Leu Trp Pro Thr Leu Ala Ala Leu Ala Leu Leu Ser Ser Val Ala

GAG GCC GCC GCC GGC GCT CGA GGC TGC CGG CTG CGG TCC CAG CTG GTG CCT GTG
Glu Ala Ala Ala Gly Ala Arg Gly Cys Arg Leu Arg Ser Gln Leu Val Pro Val

CGG GCC CTG GGC CTG GGC CAC CGG TCC GAC GAG CTG GTG CGG TTC CGG TTC TGC
Arg Ala Leu Gly Leu Gly His Arg Ser Asp Glu Leu Val Arg Phe Arg Phe Cys

TCC GGC TCC TGC CGG CGG GCC CGG TCC CCT CAC GAC CTG TCC CTG GCC TCC CTG
Ser Gly Ser Cys Arg Arg Ala Arg Ser Pro His Asp Leu Ser Leu Ala Ser Leu

CTG GGC GCC GGC GCC CTG CGG CCT CCT CCT GGC TCC CGG CCT GTG TCC CAG CCT
Leu Gly Ala Gly Ala Leu Arg Pro Pro Pro Gly Ser Arg Pro Val Ser Gln Pro

TGC TGC CGG CCT ACC CGG TAC GAG GCC GTG TCC TTC ATG GAC GTG AAC TCC ACC
Cys Cys Arg Pro Thr Arg Tyr Glu Ala Val Ser Phe Met Asp Val Asn Ser Thr

TGG CGG ACC GTG GAC CGG CTG TCC GCC ACC GCC TGC GGC TGC CTG GGC TGA
Trp Arg Thr Val Asp Arg Leu Ser Ala Thr Ala Cys Gly Cys Leu Gly •••
```

Fig. 3

```
ATG GAG CTG GGC CTG GGC GGC CTG TCC ACC CTG TCC CAC TGC CCT TGG CCT CGG
Met Glu Leu Gly Leu Gly Gly Leu Ser Thr Leu Ser His Cys Pro Trp Pro Arg

CGG CAG CCT GCC CTG TGG CCT ACC CTG GCC GCC CTG GCC CTG CTG TCC TCC GTG
Arg Gln Pro Ala Leu Trp Pro Thr Leu Ala Ala Leu Ala Leu Leu Ser Ser Val

GCC GAG GCC GCC GCC GGC GCT CGA GGC TGC CGG CTG CGG TCC CAG CTG GTG CCT
Ala Glu Ala Ala Ala Gly Ala Arg Gly Cys Arg Leu Arg Ser Gln Leu Val Pro

GTG CGG GCC CTG GGC CTG GGC CAC CGG TCC GAC GAG CTG GTG CGG TTC CGG TTC
Val Arg Ala Leu Gly Leu Gly His Arg Ser Asp Glu Leu Val Arg Phe Arg Phe

TGC TCC GGC TCC TGC CGG CGG GCC CGG TCC CCT CAC GAC CTG TCC CTG GCC TCC
Cys Ser Gly Ser Cys Arg Arg Ala Arg Ser Pro His Asp Leu Ser Leu Ala Ser

CTG CTG GGC GCC GGC GCC CTG CGG CCT CCT CCT GGC TCC CGG CCT GTG TCC CAG
Leu Leu Gly Ala Gly Ala Leu Arg Pro Pro Pro Gly Ser Arg Pro Val Ser Gln

CCT TGC TGC CGG CCT ACC CGG TAC GAG GCC GTG TCC TTC ATG GAC GTG AAC TCC
Pro Cys Cys Arg Pro Thr Arg Tyr Glu Ala Val Ser Phe Met Asp Val Asn Ser

ACC TGG CGG ACC GTG GAC CGG CTG TCC GCC ACC GCC TGC GGC TGC CTG GGC TGA
Thr Trp Arg Thr Val Asp Arg Leu Ser Ala Thr Ala Cys Gly Cys Leu Gly •••
```

Fig. 4

```
ATG AAG TGG GTG ACC TTC CTG CTG CTG CTG TTC ATC TCC GGC TCC GCC TTC TCC
Met Lys Trp Val Thr Phe Leu Leu Leu Leu Phe Ile Ser Gly Ser Ala Phe Ser

GCC GCC GGC GCT CGA GGC TGC CGG CTG CGG TCC CAG CTG GTG CCT GTG CGG GCC
Ala Ala Gly Ala Arg Gly Cys Arg Leu Arg Ser Gln Leu Val Pro Val Arg Ala

CTG GGC CTG GGC CAC CGG TCC GAC GAG CTG GTG CGG TTC CGG TTC TGC TCC GGC
Leu Gly Leu Gly His Arg Ser Asp Glu Leu Val Arg Phe Arg Phe Cys Ser Gly

TCC TGC CGG CGG GCC CGG TCC CCT CAC GAC CTG TCC CTG GCC TCC CTG CTG GGC
Ser Cys Arg Arg Ala Arg Ser Pro His Asp Leu Ser Leu Ala Ser Leu Leu Gly

GCC GGC GCC CTG CGG CCT CCT CCT GGC TCC CGG CCT GTG TCC CAG CCT TGC TGC
Ala Gly Ala Leu Arg Pro Pro Pro Gly Ser Arg Pro Val Ser Gln Pro Cys Cys

CGG CCT ACC CGG TAC GAG GCC GTG TCC TTC ATG GAC GTG AAC TCC ACC TGG CGG
Arg Pro Thr Arg Tyr Glu Ala Val Ser Phe Met Asp Val Asn Ser Thr Trp Arg

ACC GTG GAC CGG CTG TCC GCC ACC GCC TGC GGC TGC CTG GGC TGA
Thr Val Asp Arg Leu Ser Ala Thr Ala Cys Gly Cys Leu Gly •••
```

Fig. 5A

```
ATG AAG TGG GTG ACC TTC CTG CTG TTC CTG CTG TTC ATC TCC GGC GAT GCC TTC GCT
Met Lys Trp Val Thr Phe Leu Leu Phe Leu Leu Phe Ile Ser Gly Asp Ala Phe Ala

GCC GCC GGC GCT CGA GGC TGC CGG CTG CGG TCC CAG CTG GTG CCT GTG CGG GCC
Ala Ala Gly Ala Arg Gly Cys Arg Leu Arg Ser Gln Leu Val Pro Val Arg Ala

CTG GGC CTG GGC CAC CGG TCC GAC GAG CTG GTG CGG TTC CGG TTC TGC TCC GGC
Leu Gly Leu Gly His Arg Ser Asp Glu Leu Val Arg Phe Arg Phe Cys Ser Gly

TCC TGC CGG CGG GCC CGG TCC CCT CAC GAC CTG TCC CTG GCC TCC CTG CTG GGC
Ser Cys Arg Arg Ala Arg Ser Pro His Asp Leu Ser Leu Ala Ser Leu Leu Gly

GCC GGC GCC CTG CGG CCT CCT CCT GGC TCC CGG CCT GTG TCC CAG CCT TGC TGC
Ala Gly Ala Leu Arg Pro Pro Pro Gly Ser Arg Pro Val Ser Gln Pro Cys Cys

CGG CCT ACC CGG TAC GAG GCC GTG TCC TTC ATG GAC GTG AAC TCC ACC TGG CGG
Arg Pro Thr Arg Tyr Glu Ala Val Ser Phe Met Asp Val Asn Ser Thr Trp Arg

ACC GTG GAC CGG CTG TCC GCC ACC GCC TGC GGC TGC CTG GGC TGA
Thr Val Asp Arg Leu Ser Ala Thr Ala Cys Gly Cys Leu Gly •••
```

Fig. 5B

ATG GCT ACA G GTAAGCGCCCCTAAAATCCCTTTGGGCACAATGTGTCCTGAGGGGAGAGGCGGCGTCCTGT
Met Ala Thr G

AGATGGGACGGGGGCACTAACCCTCAGGTTTGGGGCTTATGAATGTTAGTATCGCCATCTAAGCCCAGTATTTG

GCCAATCTCCGAATGTTCCTGGTCCCTGGAGGGAGGCAGAGAGAGAGAGAAAAAAAAAAACCCAGCTCCTGGAA

CAGGGAGAGCGCTGGCCTCTTGCTCTCCAGCTCCCTCTGTTGCCCTCCGGTTTCTCCCCAG GC TCC CGG
                                                                                                               ly Ser Arg

ACG TCC CTG CTC CTG GCT TTT GGC CTG CTC TGC CTG TCC TGG CTT CAA GAG GGC
Thr Ser Leu Leu Leu Ala Phe Gly Leu Leu Cys Leu Ser Trp Leu Gln Glu Gly

AGT GCC GCC GCC GGC GCT CGA GGC TGC CGG CTG CGG TCC CAG CTG GTG CCT GTG
Ser Ala Ala Ala Gly Ala Arg Gly Cys Arg Leu Arg Ser Gln Leu Val Pro Val

CGG GCC CTG GGC CTG GGC CAC CGG TCC GAC GAG CTG GTG CGG TTC CGG TTC TGC
Arg Ala Leu Gly Leu Gly His Arg Ser Asp Glu Leu Val Arg Phe Arg Phe Cys

TCC GGC TCC TGC CGG CGG GCC CGG TCC CCT CAC GAC CTG TCC CTG GCC TCC CTG
Ser Gly Ser Cys Arg Arg Ala Arg Ser Pro His Asp Leu Ser Leu Ala Ser Leu

CTG GGC GCC GGC GCC CTG CGG CCT CCT CCT GGC TCC CGG CCT GTG TCC CAG CCT
Leu Gly Ala Gly Ala Leu Arg Pro Pro Pro Gly Ser Arg Pro Val Ser Gln Pro

TGC TGC CGG CCT ACC CGG TAC GAG GCC GTG TCC TTC ATG GAC GTG AAC TCC ACC
Cys Cys Arg Pro Thr Arg Tyr Glu Ala Val Ser Phe Met Asp Val Asn Ser Thr

TGG CGG ACC GTG GAC CGG CTG TCC GCC ACC GCC TGC GGC TGC CTG GGC TGA
Trp Arg Thr Val Asp Arg Leu Ser Ala Thr Ala Cys Gly Cys Leu Gly •••

NEUBLASTIN EXPRESSION CONSTRUCTS

CROSS-REFERENCE TO RELATED APPLICATIONS

This application claims priority from U.S. Provisional Patent Application No. 60/507,483, filed Oct. 2, 2003. The entire content of the prior application is incorporated herein by reference in its entirety.

TECHNICAL FIELD

The field of the invention is recombinant DNA technology and protein expression. More specifically, the invention relates to methods of producing a secreted form of neublastin.

BACKGROUND

Neublastin is a secreted protein which promotes the survival of neurons of the peripheral and central nervous system such as dopaminergic neurons (Baudet et al., 2000, *Development*, 127:4335; Roseblad et al., 2000, *Mol. Cell Neurosci.*, 15(2):199; GenBank AF120274). The gene encoding neublastin has been cloned and sequenced (Roseblad et al., 2000, *Mol. Cell Neurosci.*, 15(2):199; Baloh et al., *Neuron*, 21:1291).

Neublastin is a member of the glial cell line-derived neurotrophic factor (GDNF) ligand family. At the cellular level, GDNF members activate the receptor tyrosine kinase, RET. RET associates with a co-receptor, GDNF family receptor α (GFR α), a glycosylphosphatidyl inositol (GPI) linked membrane protein that provides ligand specificity for RET. Four GFRα's are known (GFRα1-4). Neublastin binds to GFRα3, (Baudet et al. 2000, *Development*, 127:4335; Baloh et al., 1998, *Neuron*, 21:1291) which is expressed predominantly in nociceptive sensory neurons (Orozco et al., 2001, *Eur. J. Neurosci.*, 13(11):2177). These neurons detect pain and injury. Thus, neublastin has clinical application in the general treatment of neuropathy and more specifically in the treatment of pain.

Neublastin and the other GDNF family members are distant members of the transforming growth factor β (TGF β) superfamily and thus, are characterized by the presence of seven conserved cysteine residues with similar spacing which form the structure of a cysteine knot (Saarma, 1999, *Microsc. Res. Tech.*, 45:292). The cysteine knot is comprised of a loop formed by two disulfide bridges through which a third disulfide bond passes (Rattenholl et al 2000, *J. Mol. Biol.*, 305: 523).

TGF β family members are synthesized as pre pro proteins that eventually are secreted as a mature homodimer after cleavage of the signal peptide and pro-domain (see e.g. Rattenholl, et al., 2000, *J. Mol. Biol.*, 305:523; Fairlie et al., 2001, *J. Biol. Chem.*, 276(20):16911). The signal peptide mediates secretion. The pro-domain mediates proper secretion for TGF β family members (Rattenholl et al., 2000, *J. Mol. Biol.*, 305:523; Rattenholl et al., 2001, *Eur. J. Biochem.*, 268:3296). Although macrophage inhibitory cytokine-1(MIC-1), a divergent member of the TGF β family, does not require a pro-domain for secretion, it does require the pro-domain as a quality control mechanism to ensure proper folding of the mature protein (Bootcov et al., 1997, *Proc. Natl. Acad. Sci. USA*, 94:11514). As a result, it has been widely believed that all members of the GDNF family require the pro-domain for proper folding or secretion or both.

SUMMARY

The inventors have discovered that a human neublastin polypeptide can be expressed efficiently as a pre protein rather than a pre pro protein, if the native human neublastin signal peptide is replaced with certain heterologous signal peptides.

Based on this discovery, the invention provides a method of making a secreted neublastin polypeptide. The method includes: (a) providing a eukaryotic host cell transformed with a DNA containing a nucleotide sequence that (i) encodes a secreted neublastin polypeptide operatively linked to a rat albumin signal sequence or a human growth hormone signal sequence; and (ii) does not encode a functional neublastin signal peptide or a neublastin pro-domain; and (b) culturing the host cell under conditions so that the secreted neublastin polypeptide is expressed and secreted. Preferably, the eukaryotic host cell is a mammalian cell, e.g., a Chinese hamster ovary (CHO) cell.

In some embodiments, the secreted neublastin polypeptide consists of one of the following: the 113 C-terminal amino acids of human neublastin; the 112 C-terminal amino acids of human neublastin; the 111 C-terminal amino acids of human neublastin; the 110 C-terminal amino acids of human neublastin; the 109 C-terminal amino acids of human neublastin; the 108 C-terminal amino acids of human neublastin; the 107 C-terminal amino acids of human neublastin; the 106 C-terminal amino acids of human neublastin; the 105 C-terminal amino acids of human neublastin; the 104 C-terminal amino acids of human neublastin; the 103 C-terminal amino acids of human neublastin; the 102 C-terminal amino acids of human neublastin; the 101 C-terminal amino acids of human neublastin; the 100 C-terminal amino acids of human neublastin; or the 99 C-terminal amino acids of human neublastin.

The invention also provides a nucleic acid containing a nucleotide sequence that: (i) encodes a secreted neublastin polypeptide operatively linked to a native rat albumin signal sequence, a modified rat albumin signal sequence or a human growth hormone signal sequence; and (ii) does not encode a functional neublastin signal peptide or a neublastin pro domain. The invention also provides a transformed eukaryotic host cell containing such a nucleic acid. The nucleic acid can contain, for example, (a) the nucleotide sequence of SEQ ID NO:9, SEQ ID NO:11, or SEQ ID NO:25; or (b) a nucleotide sequence encoding the polypeptides of SEQ ID NO:10, SEQ ID NO:12 or SEQ ID NO:26. In some embodiments of the invention, the nucleotide sequence encoding the secreted neublastin polypeptide and/or heterologous signal sequence is optimized for expression in a mammalian host cell.

The invention also includes a neublastin preprotein consisting of a secreted neublastin polypeptide fused to a native rat albumin signal peptide, a modified rat albumin signal peptide, or a human growth hormone signal peptide.

BRIEF DESCRIPTION OF THE DRAWINGS

FIG. 1 depicts the sequence of the 104 carboxy (C) terminal amino acids of the native human neublastin polypeptide (SEQ ID NO:1) and the corresponding DNA sequence encoding the 104 C terminal amino acids of the native human neublastin (SEQ ID NO:2) aligned with a synthetic gene encoding the 104 C terminal amino acids of the native human neublastin optimized for CHO cell expression (SEQ ID NO:3). Nucleotides in the synthetic gene that have been changed from the native sequence are indicated (*).

FIG. 2 depicts the DNA sequence (SEQ ID NO:4) and amino acid sequence (SEQ ID NO:27) of the neublastin sequence within plasmid pNBN026-35. Immediately upstream of the presented sequence is a "CT" dinucleotide that contributes to a XhoI restriction site. Immediately downstream is a BamHI restriction site.

FIG. 3 depicts the DNA (SEQ ID NO:5) and amino acid (SEQ ID NO:6) sequence of the 104 C terminal amino acids of neublastin fused to a synthetic signal sequence. The signal sequence is underlined.

FIG. 4 depicts the DNA (SEQ ID NO:7) and amino acid (SEQ ID NO:8) sequence of the 104 C terminal amino acids of neublastin fused to a neublastin signal sequence. The signal sequence is underlined.

FIG. 5A depicts the DNA (SEQ ID NO:9) and amino acid (SEQ ID NO:10) sequence of the 104 C terminal amino acids of neublastin fused to an albumin signal sequence. The signal sequence is underlined.

FIG. 5B depicts the DNA (SEQ ID NO:25) and amino acid (SEQ ID NO:26) sequence of the 104 C terminal amino acids of neublastin fused to a modified albumin signal sequence. The signal sequence (amino acids 1 to 19 of SEQ ID NO:26) is underlined.

FIG. 6 depicts the DNA sequence (SEQ ID NO:11) and amino acid sequence (SEQ ID NO:12) of the 104 C terminal amino acids of neublastin fused to a human growth hormone signal sequence. The signal sequence, which contains an intron, is underlined.

FIG. 7 depicts mass spectrometer results of neublastin secreted from CHO cells using the albumin signal sequence (7A) or the human growth hormone signal sequence (7B) (7C). The peaks at 11,156 and 11,157 daltons correspond to a 104-amino acid neublastin C terminal fragment. The peaks at 11,084 and 11,085 daltons correspond to a 103-amino acid neublastin C terminal fragment.

FIG. 9A depicts the amino acid sequence of full length neublastin including the mature protein, the pro-domain and the signal peptide (SEQ ID NO:24).

FIG. 9B depicts the amino acid sequence of the full length native neublastin signal peptide (SEQ ID NO:28).

FIG. 9C depicts the amino acid sequence of the full length neublastin pro-domain (SEQ ID NO:29).

DETAILED DESCRIPTION OF THE INVENTION

A. Definitions

Figure 7A:
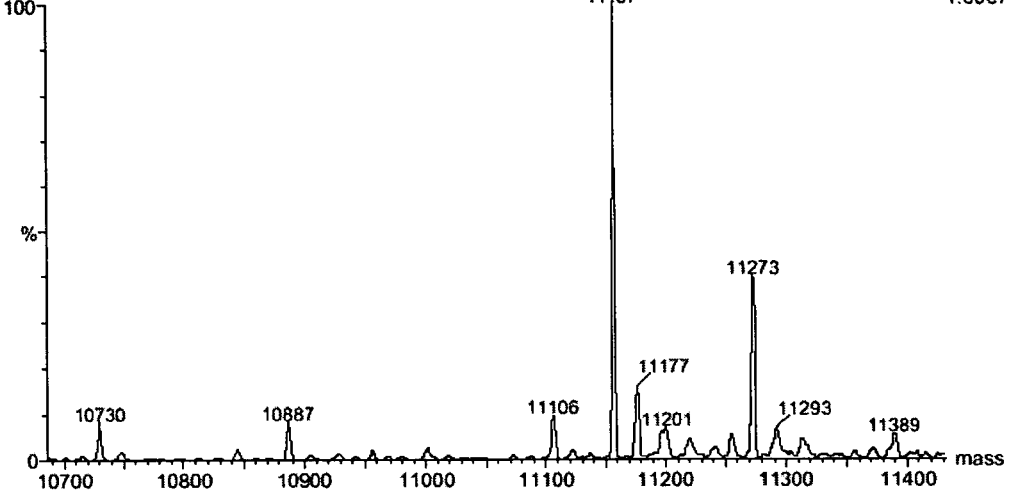
FIG. 7A depicts deglycosylated neublastin from albumin-directed secretion.

"C terminal amino acids," as used herein, means a series of contiguous amino acids in a polypeptide chain most distal from the amino (N) terminus of the polypeptide.

"Preproneublastin polypeptide," (SEQ ID NO:24) as used herein, means a polypeptide consisting of mature human neublastin, i.e., the 113 C terminal amino acids of neublastin (amino acids 108 to 220 of SEQ ID NO:24), the fill length human neublastin pro-domain, i.e., the 68 amino acids proximal to the N terminus of the mature neublastin (amino acids 40 to 107 of SEQ ID NO:24), and the human neublastin signal peptide, i.e., the 39 amino acids proximal to the N terminus of the neublastin pro-domain (amino acids 1 to 39 of SEQ ID NO:24).

"Functional neublastin signal peptide," as used herein, means amino acids 1 to 39 of SEQ ID NO:24 or any portion thereof that effects the secretion of the mature neublastin from a cell.

"Functional neublastin signal sequence" means a nucleic acid sequence encoding a functional neublastin signal peptide.

"Heterologous," as used when referring to a nucleic acid sequence or an amino acid sequence, means a sequence that originates from a source foreign to the particular host cell, or, if from the same host cell, is modified from its original form.

"Mature human neublastin polypeptide" as used herein, means the C terminal 113 amino acids of native human neublastin, i.e., amino acids 108 to 220 of SEQ ID NO:24.

"Secreted neublastin polypeptide," as used herein, means a polypeptide comprising the C terminal 99-113 amino acids of native human neublastin with up to 15 amino acid substitutions in the native sequence. In certain contexts, it will be understood that "secreted neublastin polypeptide" means a polypeptide to be secreted, as opposed to one that has been secreted already. The secreted neublastin polypeptide does not contain a functional native neublastin signal sequence or a full length neublastin pro-domain.

B. Secreted Neublastin Polypeptide

Figures 9A, 9B, 9C:
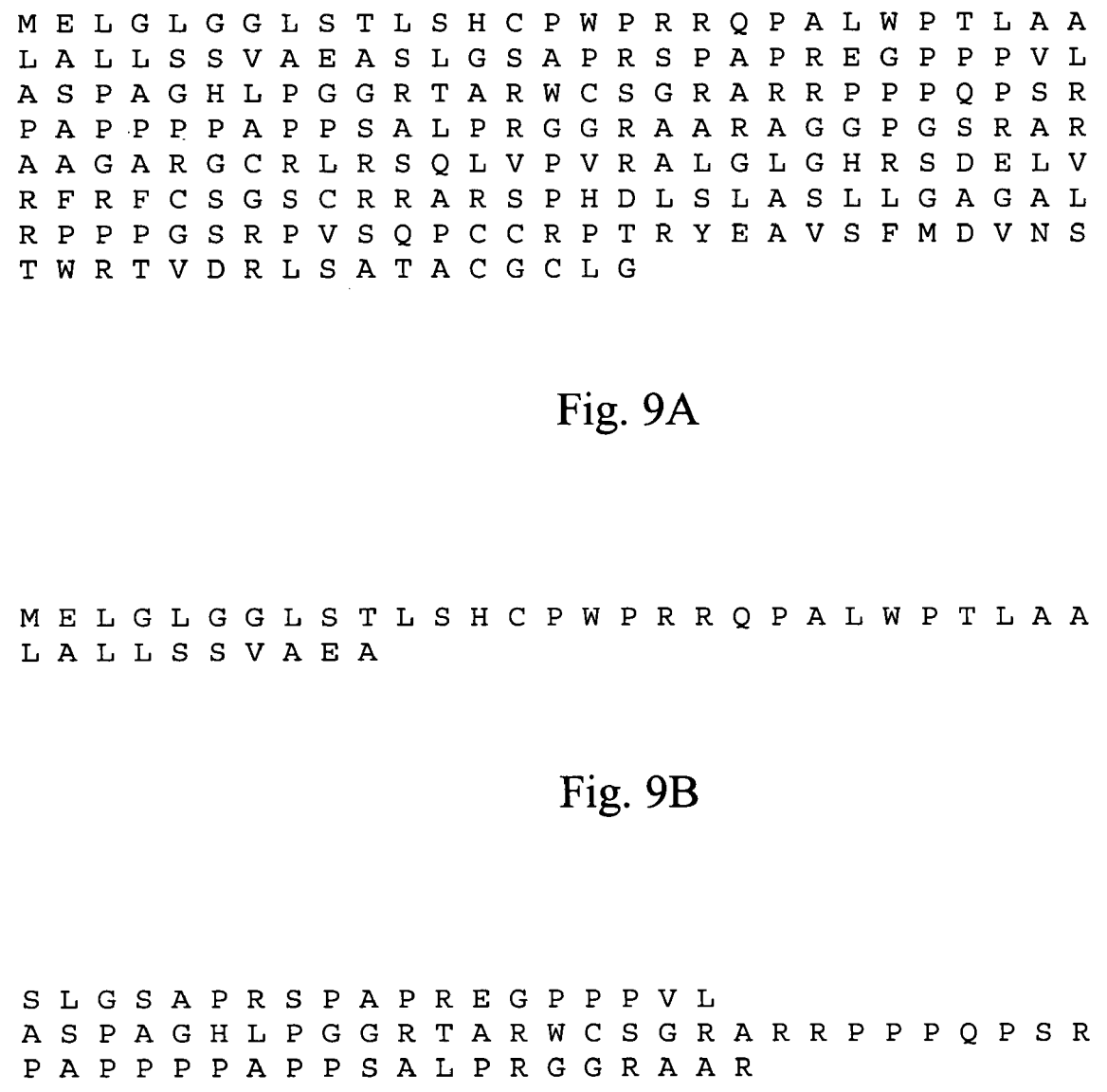

The native human pre pro neublastin polypeptide is 220 amino acids long (FIG. 9A) (SEQ ID NO:24). The neublastin signal peptide consists of 39 amino acids, beginning with methionine at position 1 and ending with alanine at position 39 (FIG. 9B). The full length pro-domain of neublastin consists of 69 amino acids, beginning with serine at position 40 and ending with arginine at position 107 (FIG. 9C). The mature neublastin polypeptide consists of the C terminal 113 amino acids, beginning with alanine at position 108 and ending with glycine at position 220. The invention provides for efficient expression of a mature human neublastin, or a biologically active truncation of a mature human neublastin, i.e., a secreted neublastin polypeptide, as a pre protein, instead of as a pre pro protein. A neublastin pre protein according to the invention generally comprises two components: a secreted neublastin polypeptide (as defined above), and a heterologous signal sequence.

Methods and nucleic acid constructs according to the invention are advantageous in at least two respects. First, a mature human neublastin polypeptide, or biologically active truncations of a mature human neublastin polypeptide, is produced in, and secreted from, cultured mammalian cells without a separate cleavage step to remove the neublastin prosequence. Second, the invention provides expression levels higher than that obtained when the human neublastin pro domain is simply removed, i.e., when the mature sequence is fused directly to the neublastin signal sequence.

The neublastin polypeptide secreted according to the invention can vary in length. Although the mature human neublastin polypeptide normally consists of the C terminal 113 amino acids of pre pro neublastin, not all of the 113 amino acids are required to achieve useful neublastin biological activity. Amino terminal truncation is permissible. Thus, the secreted neublastin polypeptide corresponds to the C terminal 99-113 amino acids of native human neublastin, i.e., its length can be 99, 100, 101, 102, 103, 104, 105, 106, 107, 108, 109, 110, 111, 112, or 113 amino acids. Selection of the exact length of the neublastin polypeptide to be secreted is a design choice, which can be made by one skilled in the art. A secreted human neublastin polypeptide consisting of the C terminal 104 amino acids of native human neublastin is exemplified in the working examples provided below. In addition to varying in length, the secreted human neublastin polypeptide can vary in sequence. As discussed in more detail below, certain amino acid substitutions can be introduced into the neublastin sequence while retaining one or more useful biological activities of native neublastin. In addition, certain mutations not normally considered "conservative" substitutions can be made, and may be desirable as a matter of protein engineering. For example, the asparagine residue at position 86 in SEQ ID NO:1 (which corresponds to position 95 in the native mature neublastin sequence), can be substituted with a lysine residue while retaining biological activity.

C. Heterologous Signal Sequence

In the present invention, a heterologous signal sequence is fused to the amino terminus of the secreted neublastin polypeptide. The inventors have discovered that certain heterologous signal sequences function surprisingly well, in contrast to the native human neublastin signal sequence, when fused to a secreted human neublastin polypeptide. According to the invention, the heterologous signal sequence can be a native rat albumin signal sequence, a modified rat signal sequence, or a human growth hormone signal sequence.

During the secretion process, the signal peptide of the neublastin pre-protein is cleaved by the host cell producing the neublastin polypeptide. While the cleavage site is generally defined, a skilled artisan will appreciate that there can be variability in the signal peptide cleavage site. Accordingly, embodiments having some ambiguity with respect to the exact cleavage site are within the scope of the invention.

In some embodiments, the secreted neublastin polypeptide is fused to a native rat albumin signal peptide. This is exemplified by SEQ ID NO:10. In other embodiments, the secreted neublastin polypeptide is linked to a modified rat albumin signal sequence. This is exemplified by SEQ ID NO:26. In other embodiments, the secreted neublastin polypeptide is fused to a human growth hormone signal sequence. This is exemplified by SEQ ID NO:12.

It will be understood by one of skill in the art that certain amino acids in a sequence of any polypeptide may be substituted for other amino acids without adversely affecting the activity of the polypeptide. Accordingly, various changes may be made in the amino acid sequences of the secreted neublastin polypeptide or DNA sequences encoding therefore without appreciable loss of their biological activity, function, or utility. Derivatives or modifications within the scope of the invention are biologically active.

Substitutes for an amino acid within the sequence of the neublastin polypeptide may be selected from other members of the class to which the amino acid belongs (see Table 1). Furthermore, various amino acids are commonly substituted with neutral amino acids, e.g., alanine, leucine, isoleucine, valine, proline, phenylalanine, tryptophan, and methionine. (See e.g. MacLennan et al., 1998, Acta Physiol. Scand. Suppl., 643:55-67; Sasaki et al., 1998, Adv. Biophys., 35:1-24). Multiple substitutions are within the scope of the invention; however, all neublastin polypeptides of the invention must possess at least one activity of native neublastin as described infra in Section C.

TABLE 1

| Original Residues | Exemplary Substitutions |
|---|---|
| Ala (A) | Val, Leu, Ile |
| Arg (R) | Lys, Gln, Asn |
| Asn (N) | Gln |
| Asp (D) | Glu |
| Cys (C) | Ser, Ala |
| Gln (Q) | Asn |
| Gly (G) | Pro, Ala |
| His (H) | Asn, Gln, Lys, Arg |
| Ile (I) | Leu, Val, Met, Ala, Phe, Norleucine |
| Leu (L) | Norleucine, Ile, Val, Met, Ala, Phe |
| Lys (K) | Arg, 1,4-Diamino-butyric Acid, Gln, Asn |
| Met (M) | Leu, Phe, Ile |
| Phe (F) | Leu, Val, Ile, Ala, Tyr |
| Pro (P) | Ala |
| Ser (S) | Thr, Ala, Cys |
| Thr (T) | Ser |
| Trp (W) | Tyr, Phe |
| Tyr (Y) | Trp, Phe, Thr, Ser |
| Val (V) | Ile, Met, Leu, Phe, Ala, Norleucine |

D. Neublastin Activity

The neublastin polypeptides produced by the methods of this invention display at least one biological activity of native neublastin. Biological activity for purposes of this invention can be determined by any suitable method. A biologically active neublastin polypeptide is a polypeptide that, when dimerized, can bind, along with GFRα3, to RET and induce RET dimerization and autophosphorylation. (See e.g. Sanicola et al., 1997, Proc. Natl. Acad. Sci. USA, 94:6238). Any method of determining receptor binding and receptor autophosphorylation may be used to evaluate the biological activity the neublastin polypeptide produced by the methods of the invention. For example, the KIRA assay (ELISA) described in Example 9 can be used to assess neublastin biological activity. (See also, Sadick et al., 1996, Anal. Biochem., 235 (2):207).

E. Nucleic Acid Constructs

A nucleic acid construct of the invention comprises a nucleic acid sequence encoding a secreted neublastin polypeptide and a heterologous signal sequence. In some embodiments, the nucleic acid construct encodes a sequence consisting of the 113 C terminal codons of the pre pro neublastin polypeptide. In certain embodiments, the nucleic acid encodes a sequence consisting of the 104 C terminal codons of the pre pro neublastin polypeptide.

In some embodiments, the nucleic acid construct encodes an albumin signal sequence, e.g., a rat albumin signal sequence, and comprises the nucleic acid sequence of SEQ ID NO:9. In some embodiments, the nucleic acid construct encodes a modified albumin signal sequence, e.g., a rat albumin signal sequence. One exemplary embodiment is a nucleic acid construct comprising SEQ ID NO:25. In other embodiments, the nucleic acid construct encodes a human growth hormone signal sequence. One exemplary embodiment is a nucleic acid construct comprising SEQ ID NO:11. The human growth hormone signal sequence may comprise an intron.

In a specific embodiment of the invention, the nucleic acid construct contains a nucleic acid sequence optimized for expression in a transfected host cell. Optimization of codon usage can be advantageous by providing increased polypeptide yield, or improved efficiency of transcription or translation. One exemplary embodiment of an optimized nucleic acid construct of the invention is set forth in SEQ ID NO:3.

Due to the known degeneracy of the genetic code, wherein more than one codon can encode the same amino acid, a DNA sequence can vary from that shown in SEQ ID NOS:9, 11, or 25 and still encode a polypeptide having the corresponding amino acid sequence of SEQ ID NOS:10, 12, or 26 respectively. Such variant DNA sequences can result from silent mutations (e.g. occurring during PCR amplification), or can be the product of deliberate mutagenesis of a native sequence, e.g., codon optimization.

The nucleic acid construct can be a vector. Examples of suitable plasmid vectors include but are not limited to pFRT/lac Zeo, pFRT/dhfr-1, (Invitrogen, Carlsbad, Calif.) pUC, pGEM and pGEX (Pharmacia, Peapack, N.J.). Other suitable vectors include viral vectors (e.g. replication defective retroviruses, adenoviruses and adeno-associated viruses), which serve equivalent functions.

Expression vectors may include one or more regulatory sequences operatively linked to the nucleic acid sequence to be expressed. Examples of regulatory sequences include promoters, enhancers, and polyadenylation signals. Such regulatory sequences are described, for example, in Goeddel, 1990 *Methods Enzymol.*, 185:3. Regulatory sequences include those which direct constitutive expression of a nucleotide sequence in many types of host cells and those which direct expression of the nucleotide sequence only in certain host cells (e.g. tissue-specific regulatory sequences). It will be appreciated by those skilled in the art that the design of the expression vector will depend on such factors as the choice of the host cell to be transformed, the level of expression of protein desired, and the like. The expression vectors of the invention can be introduced into host cells to thereby produce proteins or peptides.

Vectors used in methods of the invention may also include a nucleic acid sequence encoding a selectable marker that can be used to identify successfully transformed host cells. Suitable selectable markers for use in cultured mammalian cells include genes that confer resistance to drugs, such as neomycin, hygromycin, and methotrexate. The selectable marker may be an amplifiable selectable marker. One amplifiable selectable marker is the DHFR gene. Another suitable amplifiable marker is the DHFRr cDNA (Simonsen and Levinson, 1983, *Proc. Natl. Acad. Sci. (USA)* 80:2495). Additional selectable markers are reviewed by Thilly (*Mammalian Cell Technology*, Butterworth Publishers, Stoneham, Mass.). Suitable selectable markers can be chosen by any person skilled in the art. Selectable markers may be introduced into the host cell in the same vector as the neublastin pre sequence, or as part of a separate vector. The selectable marker and the neublastin sequence may be under the control of different promoters or the same promoter, the latter arrangement producing a dicistronic message. Constructs of this type are known in the art (see e.g. U.S. Pat. No. 4,713,339).

Expression elements employed in the invention may vary in their strength and specificities. Depending on the host/vector system utilized, any of a number of suitable transcription and translation elements, including constitutive and inducible promoters, may be used in the expression vector. When cloning in mammalian cell systems, promoters derived from the genome of mammalian cells (e.g. metallothionein promoter) or from mammalian viruses (e.g. the CMV promoter, the adenovirus late promoter; the vaccinia virus 7.5 K promoter) may be used; when generating cell lines that contain multiple copies of expression product, SV40-, BPV- and EBV-based vectors may be used with an appropriate selectable marker.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g. region E1 or E3) will result in a recombinant virus that is viable and capable of expressing peptide in infected hosts (see e.g. Logan & Shenk, 1984, *Proc. Natl. Acad. Sci. USA*, 81:3655). Alternatively, the vaccinia 7.5 K promoter may be used (see, e.g., Mackett et al., 1982, *Proc. Natl. Acad. Sci. USA*, 79:7415; Mackett et al., 1984, *J. Virol.*, 49:857; Panicali et al., 1982, *Proc. Natl. Acad. Sci. USA*, 79:4927).

Expression vectors used in the methods of the invention may also encode tags that facilitate purification of the recombinantly produced neublastin polypeptide. Examples include, but are not limited to, vector pUR278 (Ruther et al., 1983, *EMBO J.*, 2:1791) in which the coding sequences of the neublastin polypeptide described herein may be ligated into the vector in frame with the lac z coding region so that a hybrid protein is produced; pGEX vectors may also be used to express the neublastin polypeptide with a glutathione S-transferase (GST) tag. These proteins are usually soluble and can easily be purified from cells by adsorption to glutathione-agarose beads followed by elution in the presence of free glutathione. The vectors include cleavage sites (thrombin or factor Xa protease or PreScission Protease™ (Pharmacia, Peapack, N.J.)) for easy removal of the tag after purification. Other fusion tags are known in the art, e.g., histidine tags, maltose binding protein tags.

The nucleic acid constructs of the invention can be used to produce neublastin polypeptide. Eukaryotic cells may be transfected with a nucleic acid construct which encodes a recombinant neublastin polypeptide operatively linked to a heterologous signal sequence. Methods of making nucleic acid constructs and transfecting cells with the constructs are known in the art. (See e.g., Ausubel et al., eds., 1988, *Current Protocols in Molecular Biology*, Greene Publishing Associates & Wiley-Interscience: New York; Sambrook et al. 1989, *Molecular Cloning: A Laboratory Manual*, 2 ed., Cold Spring Harbor Laboratory Press: Cold Spring Harbor, N.Y.). For example, cells can be transfected using electroporation, calcium phosphate precipitation, or infection with a viral vector. In some embodiments, the transformed host cell is a mammalian cell, e.g., a CHO cell, a COS cell, a HeLa cell, or an NIH 3T3 cell.

The transformed host cells are cultured in an appropriate growth medium and under conditions such that the secreted neublastin polypeptide is expressed and secreted from the cell. An appropriate growth medium is a medium containing nutrients required for the growth of cells. Nutrients required for cell growth may include a carbon source, a nitrogen source, essential amino acids, vitamins, minerals and growth factors. Optionally, the media can contain bovine calf serum or fetal calf serum. The growth medium can be designed to select for cells containing the nucleic acid construct. This can be done, for example, by drug selection or deficiency in an essential nutrient which is complemented by the selectable marker on the nucleic acid construct or co-transfected with the nucleic acid construct. Cultured mammalian cells are sometimes grown in commercially available serum-containing or serum-free media (e.g. MEM, DMEM)(Invitrogen, Carlsbad, Calif.). Factors to be considered in the selection of a medium appropriate for the particular cell line used are known in the art.

The neublastin polypeptide may also be expressed in a transgenic animal, such as a rodent, cow, pig, sheep or goat. A transgenic animal is a non-human animal that has incorporated a foreign gene into its genome such that the foreign gene is passed from parent to offspring. Exogenous genes can be introduced into single-celled embryos (Brinster et al,. 1985, *Proc. Natl. Acad. Sci. USA*, 82:4438). Methods of producing transgenic animals are known in the art, (Wagner et al., 1981, *Proc. Natl. Acad. Sci. USA* 78:6376; McKnight et al., 1983, *Cell* 34:335; Brinster et al., 1983, *Nature* 306:332; Ritchie et al., 1984, *Nature* 312:517; Baldassarre et al., 2003, *Theriogenology* 59:831; Robl et al., 2003, *Theriogenology* 59:107; Malassagne et al., 2003, *Xenotransplantation* 10(3):267).

EXAMPLES

Example 1

Neublastin Gene Sequence Optimization

The sequence of the native human neublastin gene was examined for codon usage for optimizing expression of human neublastin in CHO cells. The codons most commonly used in CHO cells were analyzed based on data current to 2002 using a method known in the art (Nakamura et al., 1999, *Nucleic Acids Res.*, 27(1):292). The codon usage for *Cricetulus griseus* relied upon is presented in Table 2.

FIG. 1 with the changed nucleotides indicated. The two sequences are 83.33% identical.

Example 2

Cloning of the Neublastin Gene

A 100 codon (300 nucleotides) 3' form of the neublastin gene was synthesized and cloned into an expression plasmid to facilitate the insertion of various signal peptide sequences linked to the 5' codons of neublastin. The 100 codon-form of the neublastin gene was assembled by combining 40 pmol of oligonucleotides KD3-464 through KD3-469 (Table 3) in 200 µL buffer (10 mM KCl, 10 mM (NH4)2SO4, 20 mM Tris-Cl, 2 mM MgSO4, 0.1% Triton X-100, pH 8.8) containing Deep Vent Polymerase (New England BioLabs, Beverly, Mass.). The contents were heated to 95° C. for 4 minutes and cycled twenty times as follows: 95° C. for 1 minute, 60° C. for 30 seconds, and 72° C. for 1 minute, followed by an extension at 72° C. for four minutes. The termini were prepared by sequential digestion with SalI and NheI. The 330 base pair fragment, which included a non-coding region of 30 base pairs flanking the neublastin gene, was gel-purified and ligated into plasmid pFRT/dhfr-1 (a derivative of pcDNA/FRT (Invitrogen, Carlsbad, Calif.) with the hygromycin gene

TABLE 2

Frequency of codon usage in *Cricetulus* normalized per 1,000 codons.

| | | | |
|---|---|---|---|
| (Phe) UUU 19.2 | (Ser) UCU 16.0 | (Tyr) UAU 12.7 | (Cys) UGU 8.5 |
| (Phe) UUC 22.2 | (Ser) UCC 17.2 | (Tyr) UAC 16.1 | (Cys) UGC 10.0 |
| (Leu) UUA 6.0 | (Ser) UCA 10.2 | (*) UAA 0.5 | (*) UGA 1.0 |
| (Leu) UUG 14.2 | (Ser) UCG 3.5 | (***) UAG 0.5 | (Trp) UGG 12.9 |
| (Leu) CUU 13.3 | (Pro) CCU 17.5 | (His) CAU 9.5 | (Arg) CGU 5.7 |
| (Leu) CUC 18.2 | (Pro) CCC 17.7 | (His) CAC 12.7 | (Arg) CGC 9.5 |
| (Leu) CUA 7.5 | (Pro) CCA 15.4 | (Gln) CAA 10.4 | (Arg) CGA 7.0 |
| (Leu) CUG 39.0 | (Pro) CCG 4.1 | (Gln) CAG 33.2 | (Arg) CGG 10.4 |
| (Ile) AUU 17.5 | (Thr) ACU 14.5 | (Asn) AAU 17.7 | (Ser) AGU 11.5 |
| (Ile) AUC 25.5 | (Thr) ACC 21.2 | (Asn) AAC 21.1 | (Ser) AGC 16.5 |
| (Ile) AUA 6.6 | (Thr) ACA 15.6 | (Lys) AAA 24.5 | (Arg) AGA 9.5 |
| (Met) AUG 23.4 | (Thr) ACG 4.4 | (Lys) AAG 39.1 | (Arg) AGG 9.8 |
| (Val) GUU 11.3 | (Ala) GCU 22.5 | (Asp) GAU 23.9 | (Gly) GGU 13.2 |
| (Val) GUC 16.0 | (Ala) GCC 26.6 | (Asp) GAC 27.6 | (Gly) GGC 22.1 |
| (Val) GUA 8.0 | (Ala) GCA 16.7 | (Glu) GAA 27.8 | (Gly) GGA 15.9 |
| (Val) GUG 29.9 | (Ala) GCG 4.3 | (Glu) GAG 40.7 | (Gly) GGG 13.5 |

The native human nucleotide sequence encoding a C terminal 104 amino acid fragment (Roseblad et al., 2000, *Mol. Cell Neurosci.* 15(2):199; Baloh et al., *Neuron* 21:1291) and the nucleotide sequence of the synthetic gene are aligned in replaced by a dihydrofolate reductase gene) that had been gel-purified and digested with NheI and XhoI. The resulting plasmid was named pNBN026-35. The neublastin sequence within pNBN026-35 is presented in FIG. 2.

Table 3 identifies the oligonucleotides used in PCR and synthetic sequence assembly to generate signal peptide-neublastin fusion genes. Sequences are all indicated in the 5' to 3' orientation.

TABLE 3

Oligonucleotides

| Oligonucleotide Name | Oligonucleotide Sequence |
|---|---|
| KD3-464 | AAGCTTGCTAGCATGAATTCATCTCGAGGCTGCCGGCTGCGGTCCC AGCTGGTGCCTGTGCGGGCCCTGGGCCTGGGCCAC (SEQ ID NO: 13) |
| KD3-465 | TTCTGCTCCGGCTCCTGCCGGCGGGCCCGGTCCCCTCACGACCTGTC CCTGGCCTCCCTGCTGGGCGCCGGCGCCCTGCGG (SEQ ID NO: 14) |
| KD3-466 | CAGCCTTGCTGCCGGCCTACCCGGTACGAGGCCGTGTCCTTCATGG |

TABLE 3-continued

Oligonucleotides

| Oligonucleotide Name | Oligonucleotide Sequence |
|---|---|
|  | ACGTGAACTCCACCTGGCGGACCGTGGACCGGCTG<br>(SEQ ID NO: 15) |
| KD3-467 | GGCCCGCCGGCAGGAGCCGGAGCAGAACCGGAACCGCACCAGCTC<br>GTCGGACCGGTGGCCCAGGCCCAGGGCCCGCACAGG<br>(SEQ ID NO: 16) |
| KD3-468 | GTACCGGGTAGGCCGGCAGCAAGGCTGGGACACAGGCCGGGAGCC<br>AGGAGGAGGCCGCAGGGCGCCGGCGCCCAGCAGGGA<br>(SEQ ID NO: 17) |
| KD3-469 | CTTGGAATTGTCGACGGATCCTCAGCCCAGGCAGCCGCAGGCGGTG<br>GCGGACAGCCGGTCCACGGTCCGCCAGGTGGA<br>(SEQ ID NO: 18) |
| KD3-471 | AAGCTTAGCTAGCGGATCCATGAAGTGGGTGACCTTCCTGCTGCTG<br>CTGTTCATC<br>(SEQ ID NO: 19) |
| KD3-472 | GGCAGCCTCGAGCGCCGGCGGCGGAGAAGGCGGAGCCGGAGATGA<br>ACAGCAGCAGCAGGAA<br>(SEQ ID NO: 20) |
| KD3-477 | AAGCTTAGCTAGCGGATCCATGGCTACAGGTAAGC<br>(SEQ ID NO: 21) |
| KD3-479 | AAGCTTAGCTAGCGGATCCATGGAGCTGGGCCTGGGCGGCCTGTCC<br>ACCCTGTC<br>(SEQ ID NO: 22) |
| KD3-480 | GGCGGCAGCCTGCCCTGTGGCCTACCCTGGCCGCCCTGGCCCTGCT<br>GTCCTCCGT<br>(SEQ ID NO:23) |

Example 3

Construction of Signal Peptide-Neublastin Fusion

Sequences encoding four different signal peptides were tested. These included signal sequences from neublastin, rat albumin, and human growth hormone. Additionally, a synthetic signal sequence resulted from two frame-shift mutations during PCR amplification to generate the neublastin signal peptide. The fusions were synthesized using either oligonucleotide assembly or PCR. The DNA fragments were ligated into pNBN026. The relevant DNA sequence of each of the four molecules described was confirmed by DNA sequence analysis.

The synthetic signal sequence was synthesized by PCR amplification using oligonucleotides KD3-487, KD3-479, KD3-480, KD3-481, and KD3-482 (Table 3) and puReTaq polymerase (Pharmacia, Peapack, N.J.). PCR conditions included heating the reaction to 95° C. for 4 minutes and then cycling twenty times at 95° C. for 1 minute, 60° C. for 30 seconds, 72° C. for 1 minute, followed by an extension at 72° C. for four minutes. The termini were prepared by digestion with PstI and XhoI. The 330 base pair fragment was gel-purified and ligated into plasmid pNBN026 that was also gel-purified and digested with PstI- and XhoI. The resulting plasmid was named pNBN030. There were two spontaneous frameshift mutations not predicted or encoded by the oligonucleotides which compensated for each other and kept the translated protein in frame. The DNA and protein sequences are shown in FIG. 3.

The neublastin signal sequence was synthesized by PCR amplification with oligonucleotides KD3-513 and KD3-514 (Table 3). The polymerase used was puReTaq (Pharmacia, Peapack, N.J.). PCR conditions included heating to 95° C. for 4 minutes and cycling three times at 95° C. for 1 minute, 60° C. for 30 seconds, 72° C. for 1 minute, followed by an extension at 72° C. for four minutes. The termini were prepared by digestion with NheI and XhoI. The 330 base pair fragment was gel-purified and ligated into plasmid pNBN030 that was gel-purified and digested with NheI- and XhoI. The resulting plasmid was named pNBN038. The DNA and protein sequences are shown in FIG. 4.

The albumin signal sequence was synthesized by PCR amplification with oligonucleotides KD3-487, KD3-471, and KD3-472 (Table 3). The polymerase used was puReTaq (Pharmacia, Peapack, N.J.). PCR conditions included heating to 95° C. for 4 minutes and cycling twenty times at 95° C. for 1 minute, 60° C. for 30 seconds, 72° C. for 1 minute, followed by an extension at 72° C. for four minutes. The termini were prepared by digestion with PstI and XhoI. The 330 base pair fragment was gel-purified and ligated into plasmid pNBN026 that was gel-purified and digested with PstI- and XhoI. The resulting plasmid was named pNBN029. The DNA and protein sequences are shown in FIG. 5.

The human growth hormone signal sequence was synthesized by PCR amplification from plasmid pV30 (a pUC-based plasmid containing the genomic copy of the 5' end of the human growth hormone gene) with oligonucleotides KD3-487, KD3-477, and KD3-485 (Table 3). The polymerase used was puReTaq (Pharmacia, Peapack, N.J.). PCR conditions included heating to 95° C. for 4 minutes and cycling twenty times at 95° C. for 1 minute, 60° C. for 30 seconds, 72° C. for 1 minute, followed by an extension at 72° C. for four minutes. The termini were prepared by digestion with PstI and XhoI. The 330 base pair fragment was gel-purified and ligated into plasmid pNBN026 that was gel-purified and digested with PstI- and XhoI. The resulting plasmid was named pNBN031. The DNA and protein sequences are shown in FIG. 6.

Example 4

CHO Cell Transfections

CHO-DG44 cells were previously transformed with DNA sequences containing the Flp Recombination Target (frt) (A1 cells). This A1 host cell line does not contain the dihydrofolate reductase gene (DHFR) and is thus DHFR-minus. Each of the plasmids described encodes the DHFR gene, the neublastin fusion gene, plus the frt site. Plasmid pOG44 encodes the Flp recombinase gene. Cotransfection of these plasmids into A1 cells resulted in the insertion of a single copy of the signal-peptide-neublastin fusion genes and DHFR into the chromosome. A1 cells were electroporated with the plasmid of interest plus plasmid pOG44 under conditions consistent with those described by the manufacturer (i.e. 0.4 mm cuvette, 280 volts, 950 microFarads)(BioRad, Hercules, Calif.). Transformed cells expressing DHFR were selected for their ability to grow in alpha-minus medium Minimal Essential Medium-Alpha without nucleosides (Invitrogen, Carlsbad, Calif.) supplemented with 10% dialyzed fetal bovine serum (Hyclone, Logan, Utah). Approximately two weeks later, colonies were isolated and expanded into larger vessels in the same selection medium. Cell cultures were transitioned to serum-free medium and analyzed.

Example 5

Analysis of Transfected Cell Lines

Cell line candidates were screened for their ability to express neublastin. Aliquots of suspension cell cultures were centrifuged to separate cells from conditioned medium. The conditioned medium was removed from the cell pellet and both the media and the cell pellet were processed for reduced and denaturing electrophoresis on 16% polyacrylamide gels as generally described (Ausubel et al., supra). Upon completion of electrophoresis, the proteins were electroblotted onto a PVDF membrane and probed with rabbit polyclonal antiserum raised against neublastin. The antibody-Neublastin complex was detected by using a goat anti-rabbit polyclonal antiserum conjugated with horseradish-peroxidase (BioRad, Hercules, Calif.).

Protein expressed from plasmids encoding the neublastin, synthetic, albumin, and human growth hormone signal peptides each expressed immuno-reactive neublastin in the cell pellet fractions. Only the albumin and human growth hormone signal peptides, however, expressed detectable levels of neublastin in conditioned medium. The electrophoretic mobility of all expressed neublastin polypeptides was consistent with an 11 kD, 104-amino acid form of neublastin.

Example 6

Sequence of Neublastin Produced in CHO Cells

Neublastin was purified from conditioned medium using an immunoaffinity column, generally as described (Ausubel et al., supra). The amino-terminal sequence was determined from protein purified from cell lines containing the albumin and growth hormone signal peptides. Neublastin was applied onto a micro TFA filter (Applied Biosystems, Foster City, Calif.) and subjected to automated Edman degradation chemistry. Amino terminal sequencing was performed on an ABI Procise 494 sequencer. The resulting PTH amino acids were separated using an ABI 140C Microgradient system equipped with a PTH C18 reverse-phase column and analyzed using an ABI 7785A absorbance detector. For both constructs, the primary protein sequence began with the first residue of 104-amino acid C terminal fragment of full length neublastin (i.e. alanine). The neublastin preparation expressed with the growth hormone signal peptide also included a 103-amino acid neublastin C terminal fragment lacking the amino-terminal alanine residue. The 103 amino acid form of neublastin began with an alanine. In both cases, the signal peptide functioned as anticipated, i.e., the neublastin polypeptide was secreted from the cell and the signal peptide was cleaved by the cell.

Example 7

Mass Spectrometry of Recombinant Neublastin

Figure 7B:
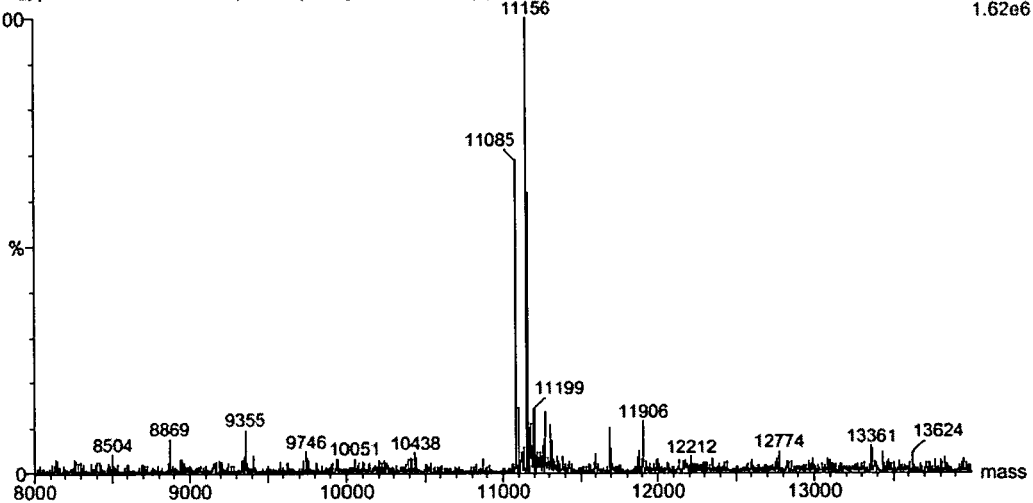
FIG. 7B depicts deglycosylated neublastin from human growth hormone-directed secretion.
Figure 7C:
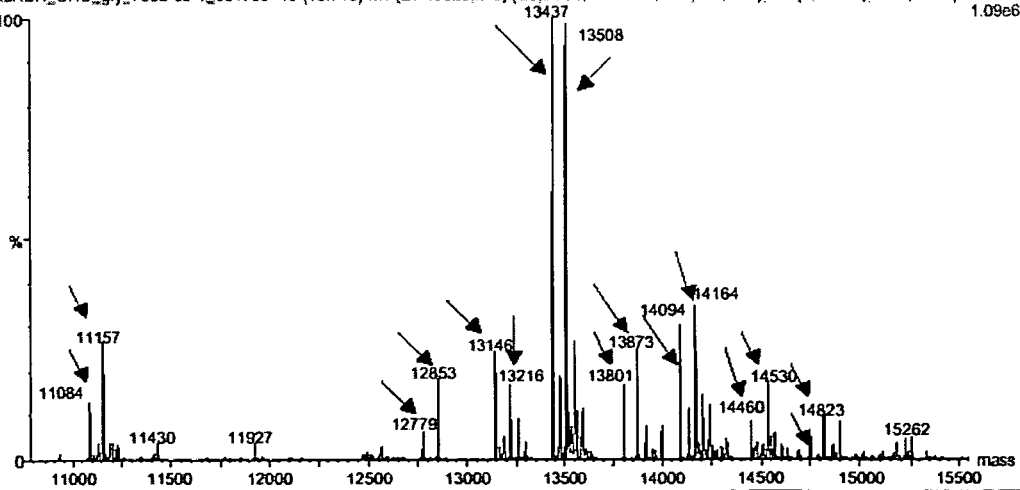
FIG. 7C depicts neublastin from human growth hormone-directed secretion. Peaks with greater masses correspond to the presence of various glycoforms.

Purified neublastin from conditioned medium of the cell lines containing constructs encoding the albumin and growth hormone signal peptides was analyzed by intact mass spectroscopy on a ZMD mass spectrometer (Waters, Milford, Mass.) as described generally by the manufacturer. For both constructs, the primary peak of deglycosylated samples corresponded to a 104-amino acid neublastin polypeptide (FIG. 7). These two signal peptides functioned as anticipated, i.e., the neublastin polypeptide was secreted from the cell and the signal peptide was cleaved by the cell. Additionally, the glycosylated neublastin secreted from cells transfected with constructs encoding neublastin and growth hormone signal peptide contained various glycoforms.

Example 8

Detection of Neublastin Activity in Media From CHO Cells Transfected With Constructs Encoding Neublastin and Heterologous Signal Sequences Biological activity was assessed using a kinase receptor activation ELISA (KIRA). The method has been previously described (Sadick et al., 1996, *Anal. Biochem.*, 1996. 235(2): 207. Briefly, NB41A3-mRL3 cells, an adherent murine neuroblastoma cell line which expresses Ret and GFRα3, were plated at $2 \times 10^5$ cells per well in 24-well plates in Dulbecco's modified eagle medium (DMEM), supplemented with 10% fetal bovine serum, and cultured for 18 hours at 37° C. and 5% $CO_2$.

The cells were washed with PBS, and treated with serial dilutions of neublastin in 0.25 mL of DMEM for 10 minutes at 37° C. and 5% $CO_2$. Each sample was analyzed in duplicate. The cells were washed with 1 mL of PBS, and lysed for 1 hour at 4° C. with 0.30 mL of 10 mM Tris HCl, pH 8.0, 0.5% Nonidet P40, 0.2% sodium deoxycholate, 50 mM NaF, 0.1 mM $Na_3 VO_4$, 1 mM phenylmethylsulfonyl fluoride while gently rocking the plates. The lysates were further agitated by repeated pipetting and 0.25 mL of sample was transferred to a 96- well ELISA plate that had been coated with 5 μg/mL of anti-Ret mAb (AA.GE7.3) (Upstate Biotechnology, Waltham, Mass.) in 50 mM carbonate buffer, pH 9.6 at 4° C. for 18 hours and then blocked at room temperature for one hour with block buffer (20 mM Tris HCl pH 7.5, 150 mM NaCl, 0.1% Tween-20 (TBST) containing 1% normal mouse serum and 3% bovine serum albumin).

After a 2 hour incubation at room temperature, the wells were washed 6 times with TBST. The plate was washed again before addition of 3,3',5,5'-tetramethylbenzidine dihydrochloride. After the color reaction, absorbance values were read at 450 nm from wells treated with lysate or lysis buffer only, and the background-corrected signal was plotted as a function of the concentration of ligand used for stimulation.

Figure 8:
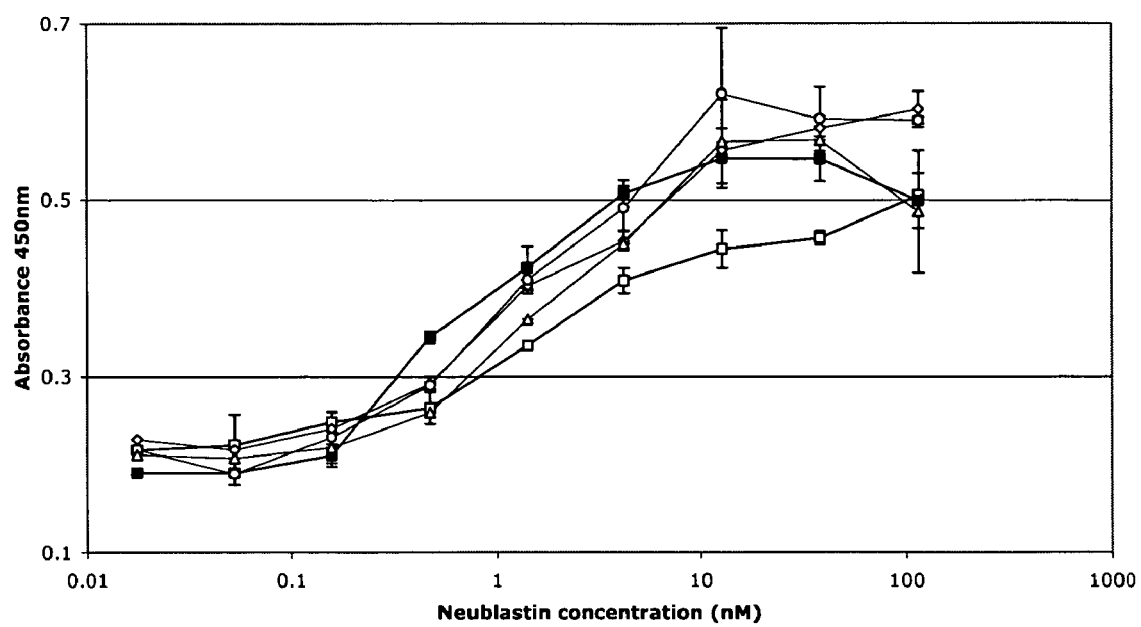
FIG. 8 depicts KIRA assay results demonstrating activity of recombinantly produced neublastin produced in CHO cells.

A series of dilutions of conditioned medium were tested and functional neublastin was detected with a profile similar to a previously demonstrated batch of neublastin expressed, purified, and refolded from E. coli (FIG. 8).

Example 9

Mature Neublastin Expressed With a Heterologous Signal Peptide

Appropriate oligonucleotides can be produced according to the method described, in Example 1, to clone a DNA sequence encoding a mature neublastin (i.e. a 113 C terminal fragment of full length neublastin). A DNA sequence encoding a signal peptide from rat albumin or human growth hormone can be fused to the DNA sequence encoding a mature neublastin polypeptide as described, in Example 2. The DNA sequence can be transfected into a eukaryotic cell, e.g., a CHO cell, to produce a secreted mature neublastin.

All references cited herein are incorporated herein by reference in their entirety. To the extent publications and patents or patent applications incorporated by reference contradict the disclosure contained in the specification, the specification is intended to supercede and/or take precedence over any such contradictory material.

Many modifications and variations of this invention can be made without departing from its spirit and scope, as will be apparent to those skilled in the art. The specific embodiments described herein are offered by way of example only and are not meant to be linmting in any way. It is intended that the specification and examples be considered as exemplary only, with a true scope and spirit of the invention being indicated by the following claims.

What is claimed is:

1. A method of making a secreted neublastin polypeptide, the method comprising:
    providing a eukaryotic host cell transformed with a DNA comprising a nucleotide sequence that encodes a secreted neublastin polypeptide lacking a functional neublastin signal peptide and a neublastin pro-domain, wherein the neublastin polypeptide is operatively linked to a signal sequence selected from the group consisting of rat albumin signal sequence and human growth hormone signal sequence, and
    culturing the eukaryotic cell under conditions so that the neublastin polypeptide is expressed and secreted.

2. The method of claim 1, wherein the eukaryotic host cell is a mammalian cell.

3. The method of claim 2, wherein the mammalian cell is a Chinese hamster ovary (CHO) cell.

4. The method of claim 1, wherein the secreted neublastin polypeptide is selected from the group consisting of:
    the 113 C-terminal amino acids of human neublastin;
    the 112 C-terminal amino acids of human neublastin;
    the 111 C-terminal amino acids of human neublastin;
    the 110 C-terminal amino acids of human neublastin;
    the 109 C-terminal amino acids of human neublastin;
    the 108 C-terminal amino acids of human neublastin;
    the 107 C-terminal amino acids of human neublastin;
    the 106 C-terminal amino acids of human neublastin;
    the 105 C-terminal amino acids of human neublastin;
    the 104 C-terminal amino acids of human neublastin;
    the 103 C-terminal amino acids of human neublastin;
    the 102 C-terminal amino acids of human neublastin;
    the 101 C-terminal amino acids of human neublastin;
    the 100 C-terminal amino acids of human neublastin; and
    the 99 C-terminal amino acids of human neublastin.

5. The method of claim 4, wherein the secreted neublastin polypeptide is the 104 C-terminal amino acids of human neublastin.

6. The method of claim 1, wherein the signal sequence is a rat albumin signal sequence.

7. The method of claim 1, wherein the signal sequence is a human growth hormone signal sequence.

8. A nucleic acid comprising a nucleotide sequence that encodes a secreted neublastin polypeptide lacking a functional neublastin signal peptide and a neublastin pro-domain, wherein the neublastin polypeptide is operatively linked to a signal sequence selected from the group consisting of a rat albumin signal sequence, the modified albumin signal sequence MKWVTFLLFLLFISGEAFA (amino acids 1 to 19 of SEQ ID NO:26), and a human growth hormone signal sequence.

9. A host cell comprising the nucleic acid of claim 8.

10. The host cell of claim 9, wherein the host cell is a mammalian cell.

11. The host cell of claim 10, wherein the mammalian cell is a CHO cell.

12. The nucleic acid of claim 8, comprising:
    the nucleotide sequence of SEQ ID NO:9, SEQ ID NO:11, or SEQ ID NO:25; or
    a nucleotide sequence encoding the polypeptide of SEQ ID NO:10, SEQ ID NO:12 or SEQ ID NO:26.

13. The nucleic acid of claim 8, wherein the nucleotide sequence has been optimized for expression in a mammalian host cell.

14. The nucleic acid of claim 8, wherein the signal sequence is a rat albumin signal sequence.

15. The nucleic acid of claim 8, wherein the signal sequence is the modified albumin signal sequence MKWVTFLLFLLFISGEAFA (amino acids 1 to 19 of SEQ ID NO:26).

16. The nucleic acid of claim 8, wherein the signal sequence is a human growth hormone signal sequence.

17. The nucleic acid of claim 8, wherein the secreted neublastin polypeptide is selected from the group consisting of:
    the 113 C-terminal amino acids of human neublastin;
    the 112 C-terminal amino acids of human neublastin;
    the 111 C-terminal amino acids of human neublastin;
    the 110 C-terminal amino acids of human neublastin;
    the 109 C-terminal amino acids of human neublastin;
    the 108 C-terminal amino acids of human neublastin;
    the 107 C-terminal amino acids of human neublastin;
    the 106 C-terminal amino acids of human neublastin;
    the 105 C-terminal amino acids of human neublastin;
    the 104 C-terminal amino acids of human neublastin;
    the 103 C-terminal amino acids of human neublastin;
    the 102 C-terminal amino acids of human neublastin;
    the 101 C-terminal amino acids of human neublastin;
    the 100 C-terminal amino acids of human neublastin; and
    the 99 C-terminal amino acids of human neublastin.

18. The nucleic acid of claim 17, wherein the secreted neublastin polypeptide is the 104 C-terminal amino acids of human neublastin.

* * * * *

UNITED STATES PATENT AND TRADEMARK OFFICE
CERTIFICATE OF CORRECTION

| | | |
|---|---|---|
| PATENT NO. | : 7,598,059 B2 | Page 1 of 1 |
| APPLICATION NO. | : 10/957221 | |
| DATED | : October 6, 2009 | |
| INVENTOR(S) | : Nels E. Pederson | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 409 days.

Signed and Sealed this
Twentieth Day of September, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,598,059 B2 | Page 1 of 1 |
| APPLICATION NO. | : 10/957221 | |
| DATED | : October 6, 2009 | |
| INVENTOR(S) | : Nels E. Pederson | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 473 days.

Signed and Sealed this
Fourth Day of December, 2012

David J. Kappos
*Director of the United States Patent and Trademark Office*

SEQUENCE LISTING

<160> NUMBER OF SEQ ID NOS: 29

<210> SEQ ID NO 1
<211> LENGTH: 104
<212> TYPE: PRT
<213> ORGANISM: Homo sapiens

<400> SEQUENCE: 1

```
Ala Ala Gly Ala Arg Gly Cys Arg Leu Arg Ser Gln Leu Val Pro Val
 1               5                  10                  15

Arg Ala Leu Gly Leu Gly His Arg Ser Asp Glu Leu Val Arg Phe Arg
            20                  25                  30

Phe Cys Ser Gly Ser Cys Arg Arg Ala Arg Ser Pro His Asp Leu Ser
        35                  40                  45

Leu Ala Ser Leu Leu Gly Ala Gly Ala Leu Arg Pro Pro Pro Gly Ser
    50                  55                  60

Arg Pro Val Ser Gln Pro Cys Cys Arg Pro Thr Arg Tyr Glu Ala Val
65                  70                  75                  80

Ser Phe Met Asp Val Asn Ser Thr Trp Arg Thr Val Asp Arg Leu Ser
                85                  90                  95

Ala Thr Ala Cys Gly Cys Leu Gly
            100
```

<210> SEQ ID NO 2
<211> LENGTH: 312
<212> TYPE: DNA
<213> ORGANISM: Homo sapiens
<220> FEATURE:
<221> NAME/KEY: CDS
<222> LOCATION: (1)...(312)

<400> SEQUENCE: 2

```
gca gcg ggg gcg cgg ggc tgc cgc ctg cgc tcg cag ctg gtg ccg gtg      48
Ala Ala Gly Ala Arg Gly Cys Arg Leu Arg Ser Gln Leu Val Pro Val
 1               5                  10                  15 cgc gcg ctc ggc ctg ggc cac cgc tcc gac gag ctg gtg cgt ttc cgc      96
Arg Ala Leu Gly Leu Gly His Arg Ser Asp Glu Leu Val Arg Phe Arg
            20                  25                  30
```

```
ttc tgc agc ggc tcc tgc cgc gcg cgc tct cca cac gac ctc agc      144
Phe Cys Ser Gly Ser Cys Arg Ala Arg Ser Pro His Asp Leu Ser
        35                  40                  45 ctg gcc agc cta ctg ggc gcc ggg gcc ctg cga ccg ccc ccg ggc tcc  192
Leu Ala Ser Leu Leu Gly Ala Gly Ala Leu Arg Pro Pro Pro Gly Ser
 50                  55                  60 cgg ccc gtc agc cag ccc tgc tgc cga ccc acg cgc tac gaa gcg gtc  240
Arg Pro Val Ser Gln Pro Cys Cys Arg Pro Thr Arg Tyr Glu Ala Val
 65                  70                  75                  80 tcc ttc atg gac gtc aac agc acc tgg aga acc gtg gac cgc ctc tcc  288
Ser Phe Met Asp Val Asn Ser Thr Trp Arg Thr Val Asp Arg Leu Ser
                 85                  90                  95 gcc acc gcc tgc ggc tgc ctg ggc                                  312
Ala Thr Ala Cys Gly Cys Leu Gly
            100

<210> SEQ ID NO 3
<211> LENGTH: 312
<212> TYPE: DNA
<213> ORGANISM: Artificial Sequence
<220> FEATURE:
<223> OTHER INFORMATION: synthetically generated sequence
<220> FEATURE:
<221> NAME/KEY: CDS
<222> LOCATION: (1)...(312)

<400> SEQUENCE: 3 gcc gcc ggc gct cga ggc tgc cgg ctg cgg tcc cag ctg gtg cct gtg  48
Ala Ala Gly Ala Arg Gly Cys Arg Leu Arg Ser Gln Leu Val Pro Val
 1               5                  10                  15 cgg gcc ctg ggc ctg ggc cac cgg tcc gac gag ctg gtg cgg ttc cgg  96
Arg Ala Leu Gly Leu Gly His Arg Ser Asp Glu Leu Val Arg Phe Arg
                 20                  25                  30 ttc tgc tcc ggc tcc tgc cgg cgg gcc cgg tcc cct cac gac ctg tcc  144
Phe Cys Ser Gly Ser Cys Arg Arg Ala Arg Ser Pro His Asp Leu Ser
        35                  40                  45 ctg gcc tcc ctg ctg ggc gcc ggc gcc ctg cgg cct cct cct ggc tcc  192
Leu Ala Ser Leu Leu Gly Ala Gly Ala Leu Arg Pro Pro Pro Gly Ser
 50                  55                  60 cgg cct gtg tcc cag cct tgc tgc cgg cct acc cgg tac gag gcc gtg  240
Arg Pro Val Ser Gln Pro Cys Cys Arg Pro Thr Arg Tyr Glu Ala Val
 65                  70                  75                  80 tcc ttc atg gac gtg aac tcc acc tgg cgg acc gtg gac cgg ctg tcc  288
Ser Phe Met Asp Val Asn Ser Thr Trp Arg Thr Val Asp Arg Leu Ser
                 85                  90                  95 gcc acc gcc tgc ggc tgc ctg ggc                                  312
Ala Thr Ala Cys Gly Cys Leu Gly
            100

<210> SEQ ID NO 4
<211> LENGTH: 303
<212> TYPE: DNA
<213> ORGANISM: Artificial Sequence
<220> FEATURE:
<223> OTHER INFORMATION: synthetically generated sequence
<220> FEATURE:
<221> NAME/KEY: CDS
<222> LOCATION: (1)...(300)

<400> SEQUENCE: 4 cga ggc tgc cgg ctg cgg tcc cag ctg gtg cct gtg cgg gcc ctg ggc  48
Arg Gly Cys Arg Leu Arg Ser Gln Leu Val Pro Val Arg Ala Leu Gly
 1               5                  10                  15
```

```
ctg ggc cac cgg tcc gac gag ctg gtg cgg ttc cgg ttc tgc tcc ggc    96
Leu Gly His Arg Ser Asp Glu Leu Val Arg Phe Arg Phe Cys Ser Gly
             20                  25                  30 tcc tgc cgg cgg gcc cgg tcc cct cac gac ctg tcc ctg gcc tcc ctg   144
Ser Cys Arg Arg Ala Arg Ser Pro His Asp Leu Ser Leu Ala Ser Leu
         35                  40                  45 ctg ggc gcc ggc gcc ctg cgg cct cct cct ggc tcc cgg cct gtg tcc   192
Leu Gly Ala Gly Ala Leu Arg Pro Pro Pro Gly Ser Arg Pro Val Ser
 50                  55                  60 cag cct tgc tgc cgg cct acc cgg tac gag gcc gtg tcc ttc atg gac   240
Gln Pro Cys Cys Arg Pro Thr Arg Tyr Glu Ala Val Ser Phe Met Asp
 65                  70                  75                  80 gtg aac tcc acc tgg cgg acc gtg gac cgg ctg tcc gcc acc gcc tgc   288
Val Asn Ser Thr Trp Arg Thr Val Asp Arg Leu Ser Ala Thr Ala Cys
                 85                  90                  95 ggc tgc ctg ggc tga                                                303
Gly Cys Leu Gly
            100

<210> SEQ ID NO 5
<211> LENGTH: 429
<212> TYPE: DNA
<213> ORGANISM: Artificial Sequence
<220> FEATURE:
<223> OTHER INFORMATION: synthetically generated sequence
<220> FEATURE:
<221> NAME/KEY: CDS
<222> LOCATION: (1)...(426)

<400> SEQUENCE: 5 atg agc tgg gcc tgg gcg gcc tgt cca ccc tgt ccc act gcc ctt ggc    48
Met Ser Trp Ala Trp Ala Ala Cys Pro Pro Cys Pro Thr Ala Leu Gly
  1               5                  10                  15 ctc ggc ggc agt gcc ctg tgg cct acc ctg gcc gcc ctg gcc ctg ctg    96
Leu Gly Gly Ser Ala Leu Trp Pro Thr Leu Ala Ala Leu Ala Leu Leu
             20                  25                  30 tcc tcc gtg gcc gag gcc gcc gcc ggc gct cga ggc tgc cgg ctg cgg   144
Ser Ser Val Ala Glu Ala Ala Ala Gly Ala Arg Gly Cys Arg Leu Arg
         35                  40                  45 tcc cag ctg gtg cct gtg cgg gcc ctg ggc ctg ggc cac cgg tcc gac   192
Ser Gln Leu Val Pro Val Arg Ala Leu Gly Leu Gly His Arg Ser Asp
 50                  55                  60 gag ctg gtg cgg ttc cgg ttc tgc tcc ggc tcc tgc cgg cgg gcc cgg   240
Glu Leu Val Arg Phe Arg Phe Cys Ser Gly Ser Cys Arg Arg Ala Arg
 65                  70                  75                  80 tcc cct cac gac ctg tcc ctg gcc tcc ctg ctg ggc gcc ggc gcc ctg   288
Ser Pro His Asp Leu Ser Leu Ala Ser Leu Leu Gly Ala Gly Ala Leu
                 85                  90                  95 cgg cct cct cct ggc tcc cgg cct gtg tcc cag cct tgc tgc cgg cct   336
Arg Pro Pro Pro Gly Ser Arg Pro Val Ser Gln Pro Cys Cys Arg Pro
            100                 105                 110 acc cgg tac gag gcc gtg tcc ttc atg gac gtg aac tcc acc tgg cgg   384
Thr Arg Tyr Glu Ala Val Ser Phe Met Asp Val Asn Ser Thr Trp Arg
        115                 120                 125 acc gtg gac cgg ctg tcc gcc acc gcc tgc ggc tgc ctg ggc              426
Thr Val Asp Arg Leu Ser Ala Thr Ala Cys Gly Cys Leu Gly
    130                 135                 140 tga                                                                429

<210> SEQ ID NO 6
<211> LENGTH: 142
<212> TYPE: PRT
```

<213> ORGANISM: Artificial Sequence
<220> FEATURE:
<223> OTHER INFORMATION: synthetically generated sequence

<400> SEQUENCE: 6

```
Met Ser Trp Ala Trp Ala Ala Cys Pro Pro Cys Pro Thr Ala Leu Gly
 1               5                  10                  15

Leu Gly Gly Ser Ala Leu Trp Pro Thr Leu Ala Ala Leu Ala Leu Leu
            20                  25                  30

Ser Ser Val Ala Glu Ala Ala Ala Gly Ala Arg Gly Cys Arg Leu Arg
        35                  40                  45

Ser Gln Leu Val Pro Val Arg Ala Leu Gly Leu Gly His Arg Ser Asp
    50                  55                  60

Glu Leu Val Arg Phe Arg Phe Cys Ser Gly Ser Cys Arg Arg Ala Arg
65                  70                  75                  80

Ser Pro His Asp Leu Ser Leu Ala Ser Leu Leu Gly Ala Gly Ala Leu
                85                  90                  95

Arg Pro Pro Pro Gly Ser Arg Pro Val Ser Gln Pro Cys Cys Arg Pro
            100                 105                 110

Thr Arg Tyr Glu Ala Val Ser Phe Met Asp Val Asn Ser Thr Trp Arg
        115                 120                 125

Thr Val Asp Arg Leu Ser Ala Thr Ala Cys Gly Cys Leu Gly
    130                 135                 140
```

<210> SEQ ID NO 7
<211> LENGTH: 432
<212> TYPE: DNA
<213> ORGANISM: Homo sapiens
<220> FEATURE:
<221> NAME/KEY: CDS
<222> LOCATION: (1)...(429)

<400> SEQUENCE: 7

```
atg gag ctg ggc ctg ggc ggc ctg tcc acc ctg tcc cac tgc cct tgg      48
Met Glu Leu Gly Leu Gly Gly Leu Ser Thr Leu Ser His Cys Pro Trp
 1               5                  10                  15 cct cgg cgg cag cct gcc ctg tgg cct acc ctg gcc gcc ctg gcc ctg      96
Pro Arg Arg Gln Pro Ala Leu Trp Pro Thr Leu Ala Ala Leu Ala Leu
            20                  25                  30 ctg tcc tcc gtg gcc gag gcc gcc gcc ggc gct cga ggc tgc cgg ctg     144
Leu Ser Ser Val Ala Glu Ala Ala Ala Gly Ala Arg Gly Cys Arg Leu
        35                  40                  45 cgg tcc cag ctg gtg cct gtg cgg gcc ctg ggc ctg ggc cac cgg tcc     192
Arg Ser Gln Leu Val Pro Val Arg Ala Leu Gly Leu Gly His Arg Ser
    50                  55                  60 gac gag ctg gtg cgg ttc cgg ttc tgc tcc ggc tcc tgc cgg cgg gcc     240
Asp Glu Leu Val Arg Phe Arg Phe Cys Ser Gly Ser Cys Arg Arg Ala
65                  70                  75                  80 cgg tcc cct cac gac ctg tcc ctg gcc tcc ctg ctg ggc gcc ggc gcc     288
Arg Ser Pro His Asp Leu Ser Leu Ala Ser Leu Leu Gly Ala Gly Ala
                85                  90                  95 ctg cgg cct cct cct ggc tcc cgg cct gtg tcc cag cct tgc tgc cgg     336
Leu Arg Pro Pro Pro Gly Ser Arg Pro Val Ser Gln Pro Cys Cys Arg
            100                 105                 110 cct acc cgg tac gag gcc gtg tcc ttc atg gac gtg aac tcc acc tgg     384
Pro Thr Arg Tyr Glu Ala Val Ser Phe Met Asp Val Asn Ser Thr Trp
        115                 120                 125 cgg acc gtg gac cgg ctg tcc gcc acc gcc tgc ggc tgc ctg ggc         429
Arg Thr Val Asp Arg Leu Ser Ala Thr Ala Cys Gly Cys Leu Gly
    130                 135                 140
```

```
tga                                                                    432

<210> SEQ ID NO 8
<211> LENGTH: 143
<212> TYPE: PRT
<213> ORGANISM: Homo sapiens

<400> SEQUENCE: 8

Met Glu Leu Gly Leu Gly Gly Leu Ser Thr Leu Ser His Cys Pro Trp
 1               5                  10                  15

Pro Arg Arg Gln Pro Ala Leu Trp Pro Thr Leu Ala Ala Leu Ala Leu
            20                  25                  30

Leu Ser Ser Val Ala Glu Ala Ala Gly Ala Arg Gly Cys Arg Leu
        35                  40                  45

Arg Ser Gln Leu Val Pro Val Arg Ala Leu Gly Leu Gly His Arg Ser
    50                  55                  60

Asp Glu Leu Val Arg Phe Arg Phe Cys Ser Gly Ser Cys Arg Arg Ala
 65                  70                  75                  80

Arg Ser Pro His Asp Leu Ser Leu Ala Ser Leu Leu Gly Ala Gly Ala
                85                  90                  95

Leu Arg Pro Pro Pro Gly Ser Arg Pro Val Ser Gln Pro Cys Cys Arg
            100                 105                 110

Pro Thr Arg Tyr Glu Ala Val Ser Phe Met Asp Val Asn Ser Thr Trp
        115                 120                 125

Arg Thr Val Asp Arg Leu Ser Ala Thr Ala Cys Gly Cys Leu Gly
    130                 135                 140

<210> SEQ ID NO 9
<211> LENGTH: 369
<212> TYPE: DNA
<213> ORGANISM: Artificial Sequence
<220> FEATURE:
<223> OTHER INFORMATION: synthetically generated sequence
<220> FEATURE:
<221> NAME/KEY: CDS
<222> LOCATION: (1)...(366)

<400> SEQUENCE: 9 atg aag tgg gtg acc ttc ctg ctg ctg ttc atc tcc ggc tcc gcc        48
Met Lys Trp Val Thr Phe Leu Leu Leu Phe Ile Ser Gly Ser Ala
 1               5                  10                  15 ttc tcc gcc gcc ggc gct cga ggc tgc cgg ctg cgg tcc cag ctg gtg   96
Phe Ser Ala Ala Gly Ala Arg Gly Cys Arg Leu Arg Ser Gln Leu Val
                20                  25                  30 cct gtg cgg gcc ctg ggc ctg ggc cac cgg tcc gac gag ctg gtg cgg  144
Pro Val Arg Ala Leu Gly Leu Gly His Arg Ser Asp Glu Leu Val Arg
            35                  40                  45 ttc cgg ttc tgc tcc ggc tcc tgc cgg cgg gcc cgg tcc cct cac gac  192
Phe Arg Phe Cys Ser Gly Ser Cys Arg Arg Ala Arg Ser Pro His Asp
        50                  55                  60 ctg tcc ctg gcc tcc ctg ctg ggc gcc ggc gcc ctg cgg cct cct cct  240
Leu Ser Leu Ala Ser Leu Leu Gly Ala Gly Ala Leu Arg Pro Pro Pro
 65                  70                  75                  80 ggc tcc cgg cct gtg tcc cag cct tgc tgc cgg cct acc cgg tac gag  288
Gly Ser Arg Pro Val Ser Gln Pro Cys Cys Arg Pro Thr Arg Tyr Glu
                85                  90                  95 gcc gtg tcc ttc atg gac gtg aac tcc acc tgg cgg acc gtg gac cgg  336
Ala Val Ser Phe Met Asp Val Asn Ser Thr Trp Arg Thr Val Asp Arg
            100                 105                 110
```

```
ctg tcc gcc acc gcc tgc ggc tgc ctg ggc tga                          369
Leu Ser Ala Thr Ala Cys Gly Cys Leu Gly
        115                 120

<210> SEQ ID NO 10
<211> LENGTH: 122
<212> TYPE: PRT
<213> ORGANISM: Artificial Sequence
<220> FEATURE:
<223> OTHER INFORMATION: synthetically generated sequence

<400> SEQUENCE: 10

Met Lys Trp Val Thr Phe Leu Leu Leu Leu Phe Ile Ser Gly Ser Ala
1               5                   10                  15

Phe Ser Ala Ala Gly Ala Arg Gly Cys Arg Leu Arg Ser Gln Leu Val
            20                  25                  30

Pro Val Arg Ala Leu Gly Leu Gly His Arg Ser Asp Glu Leu Val Arg
        35                  40                  45

Phe Arg Phe Cys Ser Gly Ser Cys Arg Arg Ala Arg Ser Pro His Asp
    50                  55                  60

Leu Ser Leu Ala Ser Leu Leu Gly Ala Gly Ala Leu Arg Pro Pro Pro
65                  70                  75                  80

Gly Ser Arg Pro Val Ser Gln Pro Cys Cys Arg Pro Thr Arg Tyr Glu
                85                  90                  95

Ala Val Ser Phe Met Asp Val Asn Ser Thr Trp Arg Thr Val Asp Arg
            100                 105                 110

Leu Ser Ala Thr Ala Cys Gly Cys Leu Gly
        115                 120

<210> SEQ ID NO 11
<211> LENGTH: 663
<212> TYPE: DNA
<213> ORGANISM: Artificial Sequence
<220> FEATURE:
<223> OTHER INFORMATION: synthetically generated sequence
<220> FEATURE:
<221> NAME/KEY: CDS
<222> LOCATION: (1)...(10)
<220> FEATURE:
<221> NAME/KEY: CDS
<222> LOCATION: (281)...(660)

<400> SEQUENCE: 11 atg gct aca g gtaagcgccc ctaaaatccc tttgggcaca atgtgtcctg            50
Met Ala Thr
1 aggggagagg cggcgtcctg tagatgggac gggggcacta accctcaggt ttggggctta   110 tgaatgttag tatcgccatc taagcccagt atttggccaa tctccgaatg ttcctggtcc   170 ctggagggag gcagagagag agagaaaaaa aaaaacccag ctcctggaac agggagagcg   230 ctggcctctt gctctccagc tccctctgtt gccctccggt ttctccccag gc tcc cgg   288
                                                        Gly Ser Arg
                                                                5 acg tcc ctg ctc ctg gct ttt ggc ctg ctc tgc ctg tcc tgg ctt caa     336
Thr Ser Leu Leu Leu Ala Phe Gly Leu Leu Cys Leu Ser Trp Leu Gln
            10                  15                  20 gag ggc agt gcc gcc gcc ggc gct cga ggc tgc cgg ctg cgg tcc cag     384
Glu Gly Ser Ala Ala Ala Gly Ala Arg Gly Cys Arg Leu Arg Ser Gln
        25                  30                  35 ctg gtg cct gtg cgg gcc ctg ggc ctg ggc cac cgg tcc gac gag ctg     432
Leu Val Pro Val Arg Ala Leu Gly Leu Gly His Arg Ser Asp Glu Leu
    40                  45                  50
```

```
gtg cgg ttc cgg ttc tgc tcc ggc tcc tgc cgg cgg gcc cgg tcc cct    480
Val Arg Phe Arg Phe Cys Ser Gly Ser Cys Arg Arg Ala Arg Ser Pro
 55                  60                  65                  70 cac gac ctg tcc ctg gcc tcc ctg ctg ggc gcc ggc gcc ctg cgg cct    528
His Asp Leu Ser Leu Ala Ser Leu Leu Gly Ala Gly Ala Leu Arg Pro
             75                  80                  85 cct cct ggc tcc cgg cct gtg tcc cag cct tgc tgc cgg cct acc cgg    576
Pro Pro Gly Ser Arg Pro Val Ser Gln Pro Cys Cys Arg Pro Thr Arg
         90                  95                 100 tac gag gcc gtg tcc ttc atg gac gtg aac tcc acc tgg cgg acc gtg    624
Tyr Glu Ala Val Ser Phe Met Asp Val Asn Ser Thr Trp Arg Thr Val
    105                 110                 115 gac cgg ctg tcc gcc acc gcc tgc ggc tgc ctg ggc tga                663
Asp Arg Leu Ser Ala Thr Ala Cys Gly Cys Leu Gly
120                 125                 130

<210> SEQ ID NO 12
<211> LENGTH: 130
<212> TYPE: PRT
<213> ORGANISM: Artificial Sequence
<220> FEATURE:
<223> OTHER INFORMATION: synthetically generated sequence

<400> SEQUENCE: 12

Met Ala Thr Gly Ser Arg Thr Ser Leu Leu Leu Ala Phe Gly Leu Leu
 1               5                  10                  15

Cys Leu Ser Trp Leu Gln Glu Gly Ser Ala Ala Ala Gly Ala Arg Gly
            20                  25                  30

Cys Arg Leu Arg Ser Gln Leu Val Pro Val Arg Ala Leu Gly Leu Gly
        35                  40                  45

His Arg Ser Asp Glu Leu Val Arg Phe Arg Phe Cys Ser Gly Ser Cys
    50                  55                  60

Arg Arg Ala Arg Ser Pro His Asp Leu Ser Leu Ala Ser Leu Leu Gly
65                  70                  75                  80

Ala Gly Ala Leu Arg Pro Pro Gly Ser Arg Pro Val Ser Gln Pro
                85                  90                  95

Cys Cys Arg Pro Thr Arg Tyr Glu Ala Val Ser Phe Met Asp Val Asn
            100                 105                 110

Ser Thr Trp Arg Thr Val Asp Arg Leu Ser Ala Thr Ala Cys Gly Cys
        115                 120                 125

Leu Gly
    130

<210> SEQ ID NO 13
<211> LENGTH: 81
<212> TYPE: DNA
<213> ORGANISM: Artificial Sequence
<220> FEATURE:
<223> OTHER INFORMATION: oligonucleotide for PCR

<400> SEQUENCE: 13
aagcttgcta gcatgaattc atctcgaggc tgccggctgc ggtcccagct ggtgcctgtg    60
cgggccctgg gcctgggcca c                                              81

<210> SEQ ID NO 14
<211> LENGTH: 81
<212> TYPE: DNA
<213> ORGANISM: Artificial Sequence
<220> FEATURE:
<223> OTHER INFORMATION: oligonucleotide for PCR
```

```
<400> SEQUENCE: 14
ttctgctccg gctcctgccg gcgggcccgg tcccctcacg acctgtccct ggcctccctg      60
ctgggcgccg gcgccctgcg g                                                81

<210> SEQ ID NO 15
<211> LENGTH: 81
<212> TYPE: DNA
<213> ORGANISM: Artificial Sequence
<220> FEATURE:
<223> OTHER INFORMATION: oligonucleotide for PCR

<400> SEQUENCE: 15
cagccttgct gccggcctac ccggtacgag gccgtgtcct tcatggacgt gaactccacc      60
tggcggaccg tggaccggct g                                                81

<210> SEQ ID NO 16
<211> LENGTH: 81
<212> TYPE: DNA
<213> ORGANISM: Artificial Sequence
<220> FEATURE:
<223> OTHER INFORMATION: oligonucleotide for PCR

<400> SEQUENCE: 16
ggcccgccgg caggagccgg agcagaaccg gaaccgcacc agctcgtcgg accggtggcc      60
caggcccagg gcccgcacag g                                                81

<210> SEQ ID NO 17
<211> LENGTH: 81
<212> TYPE: DNA
<213> ORGANISM: Artificial Sequence
<220> FEATURE:
<223> OTHER INFORMATION: oligonucleotide for PCR

<400> SEQUENCE: 17
gtaccgggta ggccggcagc aaggctggga cacaggccgg gagccaggag gaggccgcag      60
ggcgccggcg cccagcaggg a                                                81

<210> SEQ ID NO 18
<211> LENGTH: 78
<212> TYPE: DNA
<213> ORGANISM: Artificial Sequence
<220> FEATURE:
<223> OTHER INFORMATION: oligonucleotide for PCR

<400> SEQUENCE: 18
cttggaattg tcgacggatc ctcagcccag gcagccgcag gcggtggcgg acagccggtc      60
cacggtccgc caggtgga                                                    78

<210> SEQ ID NO 19
<211> LENGTH: 55
<212> TYPE: DNA
<213> ORGANISM: Artificial Sequence
<220> FEATURE:
<223> OTHER INFORMATION: oligonucleotide for PCR

<400> SEQUENCE: 19
aagcttagct agcggatcca tgaagtgggt gaccttcctg ctgctgctgt tcatc           55

<210> SEQ ID NO 20
<211> LENGTH: 61
<212> TYPE: DNA
```

```
<213> ORGANISM: Artificial Sequence
<220> FEATURE:
<223> OTHER INFORMATION: oligonucleotide for PCR

<400> SEQUENCE: 20
ggcagcctcg agcgccggcg gcggagaagg cggagccgga gatgaacagc agcagcagga      60
a                                                                     61

<210> SEQ ID NO 21
<211> LENGTH: 35
<212> TYPE: DNA
<213> ORGANISM: Artificial Sequence
<220> FEATURE:
<223> OTHER INFORMATION: oligonucleotide for PCR

<400> SEQUENCE: 21
aagcttagct agcggatcca tggctacagg taagc                                 35

<210> SEQ ID NO 22
<211> LENGTH: 54
<212> TYPE: DNA
<213> ORGANISM: Artificial Sequence
<220> FEATURE:
<223> OTHER INFORMATION: oligonucleotide for PCR

<400> SEQUENCE: 22
aagcttagct agcggatcca tggagctggg cctgggcggc ctgtccaccc tgtc            54

<210> SEQ ID NO 23
<211> LENGTH: 55
<212> TYPE: DNA
<213> ORGANISM: Artificial Sequence
<220> FEATURE:
<223> OTHER INFORMATION: oligonucleotide for PCR

<400> SEQUENCE: 23
ggcggcagcc tgccctgtgg cctaccctgg ccgccctggc cctgctgtcc tccgt           55

<210> SEQ ID NO 24
<211> LENGTH: 220
<212> TYPE: PRT
<213> ORGANISM: Homo sapiens

<400> SEQUENCE: 24

Met Glu Leu Gly Leu Gly Gly Leu Ser Thr Leu Ser His Cys Pro Trp
 1               5                  10                  15

Pro Arg Arg Gln Pro Ala Leu Trp Pro Thr Leu Ala Ala Leu Ala Leu
             20                  25                  30

Leu Ser Ser Val Ala Glu Ala Ser Leu Gly Ser Ala Pro Arg Ser Pro
         35                  40                  45

Ala Pro Arg Glu Gly Pro Pro Val Leu Ala Ser Pro Ala Gly His
     50                  55                  60

Leu Pro Gly Gly Arg Thr Ala Arg Trp Cys Ser Gly Arg Ala Arg
 65                  70                  75                  80

Pro Pro Pro Gln Pro Ser Arg Pro Ala Pro Pro Pro Ala Pro
                 85                  90                  95

Ser Ala Leu Pro Arg Gly Gly Arg Ala Ala Arg Ala Gly Pro Gly
            100                 105                 110

Ser Arg Ala Arg Ala Ala Gly Ala Arg Gly Cys Arg Leu Arg Ser Gln
        115                 120                 125

Leu Val Pro Val Arg Ala Leu Gly Leu Gly His Arg Ser Asp Glu Leu
```

```
                130                 135                 140
Val Arg Phe Arg Phe Cys Ser Gly Ser Cys Arg Arg Ala Arg Ser Pro
145                 150                 155                 160

His Asp Leu Ser Leu Ala Ser Leu Leu Gly Ala Gly Ala Leu Arg Pro
                165                 170                 175

Pro Pro Gly Ser Arg Pro Val Ser Gln Pro Cys Cys Arg Pro Thr Arg
            180                 185                 190

Tyr Glu Ala Val Ser Phe Met Asp Val Asn Ser Thr Trp Arg Thr Val
        195                 200                 205

Asp Arg Leu Ser Ala Thr Ala Cys Gly Cys Leu Gly
    210                 215                 220

<210> SEQ ID NO 25
<211> LENGTH: 372
<212> TYPE: DNA
<213> ORGANISM: Artificial Sequence
<220> FEATURE:
<223> OTHER INFORMATION: synthetically generated sequence
<220> FEATURE:
<221> NAME/KEY: CDS
<222> LOCATION: (1)...(369)

<400> SEQUENCE: 25 atg aag tgg gtg acc ttc ctg ctg ttc ctg ctg ttc atc tcc ggc gat      48
Met Lys Trp Val Thr Phe Leu Leu Phe Leu Leu Phe Ile Ser Gly Asp
1               5                   10                  15 gcc ttc gct gcc gcc ggc gct cga ggc tgc cgg ctg cgg tcc cag ctg      96
Ala Phe Ala Ala Ala Gly Ala Arg Gly Cys Arg Leu Arg Ser Gln Leu
            20                  25                  30 gtg cct gtg cgg gcc ctg ggc ctg ggc cac cgg tcc gac gag ctg gtg     144
Val Pro Val Arg Ala Leu Gly Leu Gly His Arg Ser Asp Glu Leu Val
        35                  40                  45 cgg ttc cgg ttc tgc tcc ggc tcc tgc cgg cgg gcc cgg tcc cct cac     192
Arg Phe Arg Phe Cys Ser Gly Ser Cys Arg Arg Ala Arg Ser Pro His
    50                  55                  60 gac ctg tcc ctg gcc tcc ctg ctg ggc gcc ggc gcc ctg cgg cct cct     240
Asp Leu Ser Leu Ala Ser Leu Leu Gly Ala Gly Ala Leu Arg Pro Pro
65                  70                  75                  80 cct ggc tcc cgg cct gtg tcc cag cct tgc tgc cgg cct acc cgg tac     288
Pro Gly Ser Arg Pro Val Ser Gln Pro Cys Cys Arg Pro Thr Arg Tyr
                85                  90                  95 gag gcc gtg tcc ttc atg gac gtg aac tcc acc tgg cgg acc gtg gac     336
Glu Ala Val Ser Phe Met Asp Val Asn Ser Thr Trp Arg Thr Val Asp
            100                 105                 110 cgg ctg tcc gcc acc gcc tgc ggc tgc ctg ggc tga                     372
Arg Leu Ser Ala Thr Ala Cys Gly Cys Leu Gly
        115                 120

<210> SEQ ID NO 26
<211> LENGTH: 123
<212> TYPE: PRT
<213> ORGANISM: Artificial Sequence
<220> FEATURE:
<223> OTHER INFORMATION: synthetically generated sequence

<400> SEQUENCE: 26

Met Lys Trp Val Thr Phe Leu Leu Phe Leu Leu Phe Ile Ser Gly Asp
1               5                   10                  15

Ala Phe Ala Ala Ala Gly Ala Arg Gly Cys Arg Leu Arg Ser Gln Leu
            20                  25                  30

Val Pro Val Arg Ala Leu Gly Leu Gly His Arg Ser Asp Glu Leu Val
```

```
                    35                  40                  45
Arg Phe Arg Phe Cys Ser Gly Ser Cys Arg Arg Ala Arg Ser Pro His
            50                  55                  60

Asp Leu Ser Leu Ala Ser Leu Leu Gly Ala Gly Ala Leu Arg Pro Pro
 65                  70                  75                  80

Pro Gly Ser Arg Pro Val Ser Gln Pro Cys Cys Arg Pro Thr Arg Tyr
                85                  90                  95

Glu Ala Val Ser Phe Met Asp Val Asn Ser Thr Trp Arg Thr Val Asp
                100                 105                 110

Arg Leu Ser Ala Thr Ala Cys Gly Cys Leu Gly
            115                 120
```

<210> SEQ ID NO 27
<211> LENGTH: 100
<212> TYPE: PRT
<213> ORGANISM: Artificial Sequence
<220> FEATURE:
<223> OTHER INFORMATION: synthetically generated sequence

<400> SEQUENCE: 27

```
Arg Gly Cys Arg Leu Arg Ser Gln Leu Val Pro Val Arg Ala Leu Gly
 1               5                  10                  15

Leu Gly His Arg Ser Asp Glu Leu Val Arg Phe Arg Phe Cys Ser Gly
                20                  25                  30

Ser Cys Arg Arg Ala Arg Ser Pro His Asp Leu Ser Leu Ala Ser Leu
            35                  40                  45

Leu Gly Ala Gly Ala Leu Arg Pro Pro Gly Ser Arg Pro Val Ser
 50                  55                  60

Gln Pro Cys Cys Arg Pro Thr Arg Tyr Glu Ala Val Ser Phe Met Asp
 65                  70                  75                  80

Val Asn Ser Thr Trp Arg Thr Val Asp Arg Leu Ser Ala Thr Ala Cys
                85                  90                  95

Gly Cys Leu Gly
            100
```

<210> SEQ ID NO 28
<211> LENGTH: 39
<212> TYPE: PRT
<213> ORGANISM: Homo sapiens

<400> SEQUENCE: 28

```
Met Glu Leu Gly Leu Gly Gly Leu Ser Thr Leu Ser His Cys Pro Trp
 1               5                  10                  15

Pro Arg Arg Gln Pro Ala Leu Trp Pro Thr Leu Ala Ala Leu Ala Leu
                20                  25                  30

Leu Ser Ser Val Ala Glu Ala
            35
```

<210> SEQ ID NO 29
<211> LENGTH: 68
<212> TYPE: PRT
<213> ORGANISM: Homo sapiens

<400> SEQUENCE: 29

```
Ser Leu Gly Ser Ala Pro Arg Ser Pro Ala Pro Arg Glu Gly Pro Pro
 1               5                  10                  15

Pro Val Leu Ala Ser Pro Ala Gly His Leu Pro Gly Gly Arg Thr Ala
                20                  25                  30
```

```
            -continued

Arg Trp Cys Ser Gly Arg Ala Arg Arg Pro Pro Pro Gln Pro Ser Arg
        35                  40                  45

Pro Ala Pro Pro Pro Pro Ala Pro Pro Ser Ala Leu Pro Arg Gly Gly
    50                  55                  60

Arg Ala Ala Arg
65
```